United States Patent
Hurley et al.

(10) Patent No.: US 9,549,828 B2
(45) Date of Patent: Jan. 24, 2017

(54) MODULAR PROSTHETIC SOCKETS AND METHODS FOR MAKING SAME

(71) Applicant: LIM INNOVATIONS, INC., San Francisco, CA (US)

(72) Inventors: Garrett Ray Hurley, San Francisco, CA (US); Jesse Robert Williams, San Francisco, CA (US)

(*) Notice: Subject to any disclaimer, the term of this patent is extended or adjusted under 35 U.S.C. 154(b) by 0 days.

(21) Appl. No.: 14/798,295

(22) Filed: Jul. 13, 2015

(65) Prior Publication Data
US 2015/0313730 A1     Nov. 5, 2015

Related U.S. Application Data

(63) Continuation of application No. 14/659,433, filed on Mar. 16, 2015, and a continuation of application No.
(Continued)

(51) Int. Cl.
*A61F 2/78*     (2006.01)
*A61F 2/80*     (2006.01)
(Continued)

(52) U.S. Cl.
CPC ............... *A61F 2/80* (2013.01); *A61F 2/5044* (2013.01); *A61F 2/5046* (2013.01); *A61F 2/54* (2013.01);
(Continued)

(58) Field of Classification Search
CPC ............ A61F 2/78; A61F 2/80; A61F 2/5046; A61F 2002/785
See application file for complete search history.

(56) References Cited

U.S. PATENT DOCUMENTS

| | | |
|---|---|---|
| 1,144,681 A | 6/1915 | Apgar |
| 1,893,853 A | 1/1933 | Tullis |

(Continued)

FOREIGN PATENT DOCUMENTS

| | | |
|---|---|---|
| DE | 319623 | 3/1920 |
| DE | 319623 C | 12/1920 |

(Continued)

OTHER PUBLICATIONS

Alley, "The High-Fidelity Interface: Skeletal Stabilization through Alternating Soft Tissue Compression and Release", Myoelectric Symposium 2011, New Brunswick, Canada, Aug. 14-19, 2011. (3 pages).

(Continued)

*Primary Examiner* — Bruce E Snow
(74) *Attorney, Agent, or Firm* — Merchant & Gould, P.C.

(57) ABSTRACT

The invention relates to a prosthetic socket for a residual limb of the lower extremity or upper extremity of an individual person. The residual limb has particular dimensions and anatomical contours; the prosthetic socket has dimensions and contours that fit the dimensions and contours of the residual limb. The prosthetic socket may also fit in a manner that is biomechanically particularly appropriate for the individual. The prosthetic socket is an assembly of components from groups of components that include (a) struts arranged longitudinally with respect to the residual limb, (b) proximal brim members arranged proximally to the struts and connected thereto; and (c) distal socket members disposed at the distal base of the prosthetic socket. The socket components within these groups may be modular in that they can vary with respect to dimensions and/or contours, and yet have common connecting features that permit assembly of the components together to form the prosthetic socket.

10 Claims, 20 Drawing Sheets

Related U.S. Application Data

13/675,761, filed on Nov. 13, 2012, now Pat. No. 8,978,224.

(60) Provisional application No. 61/559,051, filed on Nov. 12, 2011.

(51) Int. Cl.
*A61F 2/50* (2006.01)
*A61F 2/54* (2006.01)
*A61F 2/60* (2006.01)

(52) U.S. Cl.
CPC . *A61F 2/60* (2013.01); *A61F 2/78* (2013.01); *A61F 2002/5026* (2013.01); *A61F 2002/5027* (2013.01); *A61F 2002/5083* (2013.01); *A61F 2002/785* (2013.01); *A61F 2230/0067* (2013.01); *A61F 2230/0095* (2013.01); *Y10T 29/4978* (2015.01); *Y10T 29/49826* (2015.01)

(56) References Cited

U.S. PATENT DOCUMENTS

| | | | |
|---|---|---|---|
| 2,025,835 A | 12/1935 | Trautman | |
| 2,229,728 A * | 1/1941 | Whitfield | A61F 2/80 623/36 |
| 2,634,424 A | 4/1953 | O'Gorman | |
| 2,759,271 A | 8/1956 | Von Duyke | |
| 2,908,016 A * | 10/1959 | Botko | A61F 2/80 623/33 |
| 2,949,674 A | 8/1960 | Wexler | |
| 3,678,587 A | 7/1972 | Madden | |
| 4,161,042 A * | 7/1979 | Cottingham | A61F 2/60 623/33 |
| 4,225,982 A | 10/1980 | Cochrane et al. | |
| 4,300,245 A | 11/1981 | Saunders | |
| 4,459,709 A | 7/1984 | Leal et al. | |
| 4,704,129 A | 11/1987 | Massey | |
| 4,715,124 A | 12/1987 | Harrington | |
| 4,783,293 A | 11/1988 | Wellershaus et al. | |
| 4,842,608 A | 6/1989 | Marx et al. | |
| 4,872,879 A | 10/1989 | Shamp | |
| 4,921,502 A | 5/1990 | Shamp | |
| 4,988,360 A | 1/1991 | Shamp | |
| 5,003,969 A | 4/1991 | Azer et al. | |
| 5,014,441 A | 5/1991 | Pratt | |
| 5,108,456 A | 4/1992 | Coonan, III | |
| 5,116,382 A | 5/1992 | Steinkamp et al. | |
| 5,133,777 A | 7/1992 | Arbogast et al. | |
| 5,168,635 A | 12/1992 | Hoffman | |
| 5,201,773 A | 4/1993 | Carideo, Jr. | |
| 5,201,775 A | 4/1993 | Arbogast et al. | |
| 5,246,464 A | 9/1993 | Sabolich | |
| 5,312,669 A | 5/1994 | Bedard | |
| 5,503,543 A | 4/1996 | Laghi | |
| 5,520,529 A | 5/1996 | Heckel | |
| 5,529,575 A | 6/1996 | Klotz | |
| 5,529,576 A | 6/1996 | Lundt et al. | |
| 5,651,792 A | 7/1997 | Telikicherla | |
| 5,652,053 A | 7/1997 | Liegeois | |
| 5,718,925 A | 2/1998 | Kristinsson et al. | |
| 5,728,165 A | 3/1998 | Brown, Sr. | |
| 5,800,565 A | 9/1998 | Biedermann | |
| 5,824,111 A | 10/1998 | Schall et al. | |
| 5,885,509 A | 3/1999 | Kristinsson | |
| 5,888,215 A | 3/1999 | Roos et al. | |
| 5,888,217 A | 3/1999 | Siemker | |
| 6,033,440 A | 3/2000 | Schall et al. | |
| 6,051,026 A | 4/2000 | Biedermann et al. | |
| 6,206,932 B1 | 3/2001 | Johnson | |
| 6,228,124 B1 | 5/2001 | Slemker et al. | |
| 6,231,618 B1 | 5/2001 | Schall et al. | |
| 6,368,357 B1 | 4/2002 | Schon et al. | |
| 6,444,282 B1 | 9/2002 | Shirer | |
| 6,458,163 B1 | 10/2002 | Slemker et al. | |
| 6,497,028 B1 | 12/2002 | Rothschild et al. | |
| 6,500,210 B1 | 12/2002 | Sabolich et al. | |
| 6,576,022 B2 | 6/2003 | Meyer et al. | |
| 6,669,736 B2 | 12/2003 | Slemker et al. | |
| 6,700,563 B1 | 3/2004 | Koizumi | |
| 6,761,743 B1 | 7/2004 | Johnson | |
| 6,974,484 B2 | 12/2005 | Caspers | |
| 7,090,700 B2 | 8/2006 | Curtis | |
| 7,105,122 B2 | 9/2006 | Karason | |
| 7,172,714 B2 | 2/2007 | Jacobson | |
| 7,240,414 B2 | 7/2007 | Taylor, Sr. | |
| 7,300,466 B1 | 11/2007 | Martin | |
| 7,318,504 B2 | 1/2008 | Vitale et al. | |
| 7,338,532 B2 | 3/2008 | Haberman et al. | |
| 7,344,567 B2 | 3/2008 | Slemker | |
| 7,402,265 B2 | 7/2008 | Jacobson | |
| 7,479,163 B2 | 1/2009 | Slemker et al. | |
| 7,591,857 B2 | 9/2009 | Slemker et al. | |
| 7,658,720 B2 | 2/2010 | Johnson | |
| 7,753,866 B2 | 7/2010 | Jackovitch | |
| 7,762,973 B2 | 7/2010 | Einarsson et al. | |
| 7,980,921 B2 | 7/2011 | Saravanos | |
| 7,985,192 B2 | 7/2011 | Sheehan et al. | |
| 8,083,807 B2 | 12/2011 | Auberger et al. | |
| 8,088,320 B1 | 1/2012 | Bedard | |
| 8,116,900 B2 | 2/2012 | Slemker et al. | |
| 8,142,517 B2 | 3/2012 | Horie | |
| 8,303,527 B2 | 11/2012 | Joseph | |
| 8,323,353 B1 | 12/2012 | Alley et al. | |
| 8,382,852 B2 | 2/2013 | Laghi | |
| 8,403,993 B2 | 3/2013 | Aram et al. | |
| 8,470,050 B2 | 6/2013 | Dillingham | |
| 8,535,389 B2 | 9/2013 | McKinney | |
| 8,576,250 B2 | 11/2013 | Sabiston et al. | |
| 2002/0099450 A1 | 7/2002 | Dean et al. | |
| 2003/0181990 A1 | 9/2003 | Phillips | |
| 2004/0158332 A1 | 8/2004 | Carstens | |
| 2004/0204771 A1 | 10/2004 | Swanson, Sr. | |
| 2004/0260402 A1 | 12/2004 | Baldini et al. | |
| 2006/0009860 A1 | 1/2006 | Price, Jr. | |
| 2006/0020348 A1 | 1/2006 | Slemker et al. | |
| 2006/0020349 A1 | 1/2006 | Slemker | |
| 2007/0004993 A1 | 1/2007 | Coppens et al. | |
| 2007/0078523 A1 | 4/2007 | Kholwadwala et al. | |
| 2007/0152379 A1 | 7/2007 | Jacobson | |
| 2007/0298075 A1 | 12/2007 | Borgia et al. | |
| 2008/0269914 A1 | 10/2008 | Coppens et al. | |
| 2009/0036999 A1 | 2/2009 | Egilsson et al. | |
| 2009/0076625 A1 | 3/2009 | Groves et al. | |
| 2009/0105844 A1 | 4/2009 | Ortiz | |
| 2009/0240344 A1 | 9/2009 | Colvin et al. | |
| 2009/0299490 A1 | 12/2009 | Summit | |
| 2010/0036300 A1 | 2/2010 | Sheehan et al. | |
| 2010/0036505 A1 | 2/2010 | Hassler | |
| 2010/0082116 A1 | 4/2010 | Johnson et al. | |
| 2010/0160722 A1 | 6/2010 | Kuyava et al. | |
| 2010/0274364 A1 | 10/2010 | Pacanowsky et al. | |
| 2011/0029096 A1 | 2/2011 | Laghi | |
| 2011/0071647 A1 | 3/2011 | Mahon | |
| 2011/0114635 A1 | 5/2011 | Sheehan | |
| 2011/0160871 A1 | 6/2011 | Boone et al. | |
| 2011/0232837 A9 | 9/2011 | Ottleben | |
| 2011/0320010 A1 | 12/2011 | Vo | |
| 2012/0022667 A1 | 1/2012 | Accinni et al. | |
| 2012/0041567 A1 | 2/2012 | Cornell | |
| 2012/0101417 A1 | 4/2012 | Joseph | |
| 2012/0101597 A1 | 4/2012 | Bache | |
| 2012/0143077 A1 | 6/2012 | Sanders et al. | |
| 2012/0165956 A1 | 6/2012 | Li | |
| 2012/0191218 A1 | 7/2012 | McCarthy | |
| 2012/0215324 A1 | 8/2012 | King | |
| 2012/0253475 A1 | 10/2012 | Kelley et al. | |
| 2012/0271210 A1 | 10/2012 | Galea et al. | |
| 2012/0271433 A1 | 10/2012 | Galea et al. | |
| 2012/0293411 A1 | 11/2012 | Leithinger et al. | |
| 2013/0123940 A1 | 5/2013 | Hurley et al. | |
| 2013/0192071 A1 | 8/2013 | Esposito et al. | |
| 2013/0197318 A1 | 8/2013 | Herr et al. | |
| 2013/0245785 A1 | 9/2013 | Accini et al. | |

(56) References Cited

U.S. PATENT DOCUMENTS

| | | |
|---|---|---|
| 2013/0282141 A1 | 10/2013 | Herr et al. |
| 2014/0005801 A1 | 1/2014 | Van der Watt et al. |
| 2014/0031953 A1 | 1/2014 | MacKenzie |
| 2014/0121783 A1 | 5/2014 | Alley |
| 2014/0149082 A1 | 5/2014 | Sanders et al. |
| 2014/0277585 A1 | 9/2014 | Kelley et al. |
| 2015/0168943 A1 | 6/2015 | Hurley et al. |

FOREIGN PATENT DOCUMENTS

| | | |
|---|---|---|
| EP | 0204407 A2 | 12/1986 |
| EP | 1433447 A2 | 6/2004 |
| GB | 127451 A | 6/1919 |
| GB | 2080114 A | 2/1982 |
| WO | 91/16019 | 10/1991 |
| WO | 98/12994 | 4/1998 |
| WO | 00/03665 | 1/2000 |
| WO | 00/30572 | 6/2000 |
| WO | 2007/035875 | 3/2007 |
| WO | 2008/116025 | 9/2008 |
| WO | 2009/093020 | 7/2009 |
| WO | 2012/021823 | 2/2012 |
| WO | 2014/004709 | 1/2014 |
| WO | 2014/068269 A1 | 5/2014 |

OTHER PUBLICATIONS

Andrysek, "Lower-limb prosthetic technologies in the developing world: A review of literature from 1994-2010", Prosthetics and Orthotics International, Cardiff, Wales, UK; Dec. 2010; 34(4): pp. 378-398. (21 pages).

Burgess, et al., "The Management of Lower-Extremity Amputations: Surgery: Immediate Postsurgical Prosthetic Fitting: Patient Care", Superintendent of Documents, U.S. Government Printing Office, Washington DC 20402 Publication prepared for the Prosthetic and Sensory Aids Service, Dept. of Medicine and Surgery, Veterans Administration, Washington, D.C., Aug. 1969. (129 pages).

Conn, "Materials Science: A Look at Some of the Substances on the Market for Device Fabrication", O&P Almanac, Jun. 2012, pp. 28-31; downloaded from http://www.allardusa.com/pdf/articles/Materials%20Science%20Article%20-%20June%202012%20O%26P%20Almanac.pdf. (4 pages).

Fairley, M. "M.A.S. Socket: A Transfemoral Revolution", The O&P Edge, Jun. 2004; downloaded from www.oandp.com/articles/2004-06-03.asp. (4 pages).

Fairley, "From Academia to the Developing World: Student Engineers Create Collaborative Technologies", The O&P Edge Magazine, Oandp.com, (May 2011) pp. 1-3.

Filauer LLC and Centri, "COMFIL—Thermo Formable Composite Technique", Fillauer Fabrication Manuel, (Jun. 15, 2012) pp. 1-16.

Gard, S.A. "Overview of Lower Limb Prosthetics Research", WRAMC and the VA Orthopedic & Prosthetic Workshop, Arlington, VA, Nov. 17 and 18, 2003, pp. 1-48. (49 pages).

Geil, M.D. "Consistency, precision, and accuracy of optical and electromagnetic shape-capturing systems for digital measurement of residual-limb anthropometrics of persons with transtibial amputation", Journal of Rehabilitation Research and Development, vol. 44, No. 4 (2007); pp. 515-524, U.S.A. (10 pages).

Gerschutz, et al., "Mechanical Evaluation of Direct Manufactured Prosthetic Sockets", American Academy of Orthotists & Prosthetists, 38th Academy Annual Meeting and Scientific Symposium, U.S.A., Mar. 21-24, 2012; downloaded from http://www.oandp.org/publications/jop/2012/2012-19.pdf. (1 page).

Gleave, "A Plastic Socket and Stump Casting Technique for Above-Knee Prostheses", Orthopaedic and Prosthetic Appliance Department, Hong Kong Government Medical Department, The Journal of Bone and Joint Surgery, vol. 47B, No. 1, (Feb. 1965) pp. 1-3.

Greenwald, et al., "Volume Management: Smart Variable Geometry Socket (SVGS) Technology for Lower-Limb Prostheses", JPO Journal of Prosthetics and Orthotics, vol. 15, No. 3 (2003), pp. 107-112, U.S.A. (6 pages).

Hong, et al, "Dynamic Moisture Vapor Transfer through Textiles: Part I: Clothing Hygrometry and the Influence of Fiber Type", Textile Research Journal, Thousand Oaks, California, U.S.A., Dec. 1988; 58: 697-706, Abstract. (1 page).

Hwang, "Blooming Winner—Spark!", Spark Galleries, 2012/Spark/Concept, Spark Design Awards, (2012) p. 1.

Jana, "Designing a Cheaper, Simpler Prosthetic Arm", ZDNet, (Nov. 14, 2011) pp. 1-3.

Koike, et al., "The TC Double Socket Above-knee Prosthesis", Prosthetics and Orthotics International, vol. 5, Tokyo Metropolitan Rehabilitation Center for the Physically and Mentally Handicapped, (1981) pp. 129-134.

Krouskop, et al., "Computer-aided design of a prosthetic socket for an above-knee amputee", Journal of Rehabilitation Research and Development, vol. 24, No. 2 (Spring 1987) pp. 31-38, U.S.A. (8 pages).

Manucharian, "An Investigation of Comfort Level Trend Differences Between the Hands-On Patellar Tendon Bearing and Hands-Off Hydrocast Transtibial Prosthetic Sockets", JPO: Journal of Prosthetics and Orthotics, Washington, D.C., U.S.A.; vol. 23, No. 3, 2011: pp. 124-140. (17 pages).

Otto Bock Healthcare LLP, "Initial and Interim Prostheses", Otto Bock Healthcare LLP, Prosthetics Lower Extremities 2008, (Feb. 2013) pp. 1-8, www.ottobockus.com/cps/rde/xbcr/ob_us_en/08cat_1.pdf.

Otto Bock Healthcare LLP , "Ottobock: PU Resin Kit Polytol"; downloaded Dec. 17, 2012 from http://www.ottobock.com/cps/rde/xchg/ob_com_en/hs.xsl/17414.html. (2 pages).

Sanders, et al., "Residual limb volume change: Systematic review of measurement and management", Journal of Rehabilitation Research & Development, 2011, vol. 48: pp. 949-986, U.S.A. (29 pages).

Sathishkumar, et al., "A cost-effective, adjustable, femoral socket, temporary prosthesis for immediate rehabilitation of above-knee amputation", International Journal of Rehabilitation Research, Ljubljana, Slovenia, Mar. 2004, vol. 7, Issue 1; pp. 71-74, abstract. (1 page).

SBIR topic summary: "Pro-Active Dynamic Accommodating Socket", SITIS archives topic No. OSD08-H18 (OSD); http://www.dodsbir.net/sitis/archieves_display_topic.asp?Bookmark=34570; downloaded and printed Mar. 25, 2013, U.S. A. (4 pages).

Smith, "Silver Linings for O&P Devices", The Academy Today, vol. 1, No. 4: Oct. 2005; downloaded from http://www.oandp.org/AcademyTODAY/2005Oct/7.asp. (4 pages).

Spaeth, JP , "Laser imaging and computer-aided design and computer-aided manufacture in prosthetics and orthotics", Physical Medicine and Rehabilitation Clinics of North America, Elsevier Publishing, Amsterdam, The Netherlands; Feb. 2006 17(1): 245-263, abstract. (2 pages).

Turner, "FIT for Everyone", Yanko Design—Form Beyond Junction, (Jul. 17, 2015) pp. 1-3.

Unknown Author "Hanger ComfortFlex Socket System for Prosthetic Devices:" website pages downloaded Nov. 28, 2012 from http://www.hanger.com/prosthetics/services/Technology/Pages/ComfortFlex.aspx. pp. 1-2.

Wilson Jr. "A Material for Direct Forming of Prosthetic Sockets", downloaded from http://www.oandplibrary.org/al/1970_01_053.asp; downloaded Dec. 14, 2012. (4 pages).

Wilson, "Recent Advances in Above-Knee Prosthetics", Artificial Limbs, vol. 12, No. 2, (1968), pp. 1-27.

Wu, et al, "CIR sand casting system for trans-tibial socket", Prosthet Orthol Int. Aug. 2003: 27(2): 146-52, abstract. (1 page).

Notification of the First Office Action issued by the State Intellectual Property Office of the People's Republic of China in connection with Chinese Application No. 2012-80066479.8, (May 26, 2015) pp. 1-9.

Extended Search Report issued by the European Patent Office for European Patent Application No. 12847452.5, (Jul. 21, 2015) pp. 1-7.

(56) References Cited

OTHER PUBLICATIONS

International Search Report issued by the US Patent Office for International Application No. PCT/US2012/064876,(Feb. 19, 2013) pp. 1-6.
Written Opinion issued by the US Patent Office for International Application No. PCT/US2012/064876, (Feb. 19, 2013) pp. 1-10.
International Search Report issued by the US Patent Office for International Application No. PCT/US2014/029773, (Jun. 13, 2014) pp. 1-14.
Written Opinion, for International issued by the US Patent Office for International Application No. PCT/US2014/029773, (Jun. 13, 2014) pp. 1-14.
International Search Report issued by the Australian Patent Office for International Application No. PCT/US2014/043500, (Aug. 14, 2014) pp. 1-13.
Written Opinion of the International Searching Authority issued by the Australian Patent Office for International Application No. PCT/US2014/043500, (Aug. 18, 2014) pp. 1-8.
International Search Report issued by the US Patent Office for International Application No. PCT/US15/021611, (Jun. 25, 2015) pp. 1-2.
Written Opinion of the Searching Authority issued by the US Patent Office for International Application No. PCT/US15/021611, (Jun. 25, 2015) pp. 1-4.
International Search Report issued by the US Patent Office for International Application No. PCT/US2014/070666, (Mar. 31, 2015) pp. 1-2.
Written Opinion of the Searching Authority issued by the US Patent Office for International Application No. PCT/US2014/070666, (Mar. 31, 2015) pp. 1.
Supplemental European Search Report for related European Patent Application No. 12847452.5, mailed Jul. 21, 2015 (7 pages).
Compton, Compton table. "New plastics for forming directly on the patient." Prosthetics and Orthotics International, 1978, vol. 2, No. 1, pp. 43-47.
Fairley, Miki. Socket can be fabricated, modified, fitted-in one hour. O&P Edge Magazine. Jun. 2007.
Allard. Cut-4-Custom: Custom TLSO in less than an hour. O&P Edge Magazine. Jul. 2010.
INSTAMORPH. Remoldable prosthetics. Apr. 2013. <www.instamorph.com/ideas/outdoors-and-ergonomics/remoldable-prosthetics>.
Kelley et al. U.S. Appl. No. 61/794,948, filed Mar. 15, 2013.
First European Examination Report for European Patent Application No. 12847452.5, dated Sep. 13, 2016 (4 pages).
Supplemental European Search Report for European Patent Application No. 14770297.1, dated Sep. 19, 2016 (6 pages).

* cited by examiner

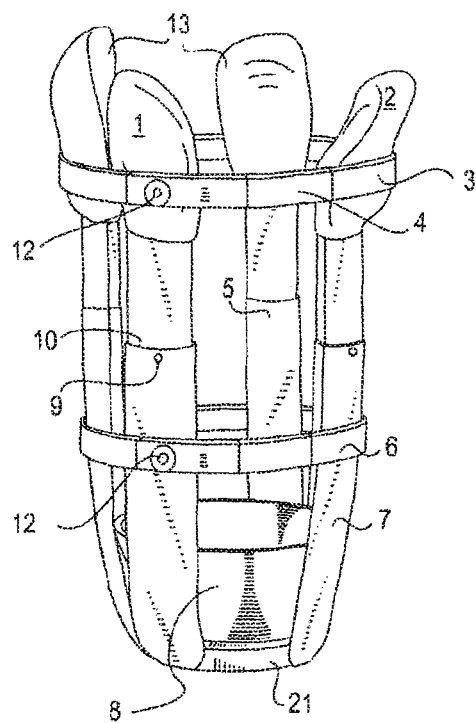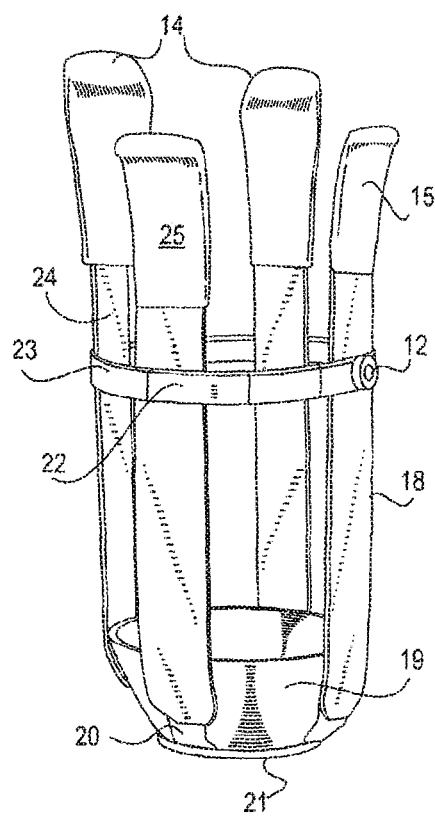
FIG. 1
FIG. 2

MODULAR PROSTHETIC SOCKETS AND METHODS FOR MAKING SAME

CROSS-REFERENCE TO RELATED APPLICATION(S)

This application is a continuation application of Ser. No. 14/659,433, filed Mar. 16, 2015 entitled "Modular Prosthetic Sockets and Methods for Making Same," which is a continuation application of Ser. No. 13/675,761, filed Nov. 13, 2012, now U.S. Pat. No. 8,978,224, entitled "Modular Prosthetic Sockets and Methods for Making Same," which claims the benefit of U.S. Provisional Patent Application No. 61/559,051, filed on Nov. 12, 2011, entitled "Method for Making a Prosthetic Socket, a Modular System and Resultant Product of the Process." The disclosures of all the above-referenced patent applications are hereby fully incorporated by reference.

TECHNICAL FIELD

The present invention relates to the field of prosthetics and orthotics. More particularly, the present invention relates to prosthetic sockets that are part of a prosthesis that is made to fit the residual limb of an amputee.

BACKGROUND ART

Current prosthetic limbs for the upper and lower extremity typically include a residual limb socket, an alignment system, and a functional component such as a knee, foot, or hand. For any prosthetic limb, a prosthetic socket is the portion of the prosthesis that is designed to fit and interface the residual limb with the rest of the prosthetic components. The socket is the structural component of the prosthesis that contains the residual limb, and provides connection to the other components. The prosthetic socket is an important part of the prosthetic limb; if it does not operate properly, utility of the distal components can be severely compromised.

Positive and negative molds of the residual limb typically play a central role in the making a residual limb prosthetic socket. For example, after a professional prosthetist has fully evaluated a patient's condition and needs, the prosthetist casts a negative mold of the residual limb using plaster or fiberglass casting tape. This negative mold is filled with Plaster of Paris and allowed to harden. The negative cast is then peeled off to reveal the newly formed positive mold. This positive mold may then modified by the prosthetist in an attempt to create a positive form that supports the creation of a limb socket that distributes pressure optimally on the residual when the socket is worn. The actual prosthetic socket is then fabricated over this positive mold. The positive mold is broken and removed from the fabricated socket, and the prosthetic socket may then be cut or further modified to fit its intended location and buffed.

In addition to the aspects of fabrication process just described, additional steps of the fabrication process may include making and integrating flexible inner liners, locking mechanisms, alignment mechanisms, and other components to create the final prosthetic socket product.

When complete, the socket is typically tested on the patient for fit and for the patient's subjective sense of how it feels. In spite of modifications that are possible, and in spite of level of optimization made possible by liners and locking and alignment mechanisms, the form, as provided by the positive mold and as reflected in the resultant socket dominate variables associated with the fit of the socket and patient satisfaction. By this conventional fabrication approach, the degree of possible modification of the limb socket to optimize the fit of the residual limb socket is actually quite limited. Accordingly, it is common practice to make a number of "check sockets" or "diagnostic sockets" from which the best option is chosen as the final product for the patient.

As may be understood from the foregoing brief summary of a conventional prosthetic fabrication process, there are aspects of the process that are less than satisfactory, largely associated with the centrality of physical molds within the process that transfer size and shape information from the residual limb that is reflected in the final prosthetic socket product. The process is drawn out and time consuming, and inexact. And the product, when formed and however satisfactory, is substantially fixed in form, and not readily modifiable. The residual limb, itself, is not fixed in form, and may vary in shape and condition with time as the patient ages, and as the residual limb changes in response to use and environmental conditions. Developments in the field that could improve these shortcomings would be welcome in the medical market, particularly in areas of the developing world where patients with amputated limbs are medically underserved and resources are limited.

DISCLOSURE OF INVENTION

The disclosed technology, as summarized below, relates to a prosthetic socket for the residual limb of a person who has had an amputation of a portion of an extremity. A prosthetic socket is a structure that engages the residual limb, and provides a functional base for other components, to build out a more complete a prosthetic apparatus. Embodiments of the technology relate to the prosthetic socket structure, to systems and kits from which a prosthetic socket can be assembled, to larger systems or devices that include the prosthetic socket, and to methods of making a prosthetic socket.

Embodiments of the invention may include any one or more particular aspects. For example, embodiments may include a modular aspect, wherein the prosthetic socket includes, and may be assembled from modular components. Modularity generally refers to component parts that have features that vary in dimension or shape, but nevertheless have attachment features in common that provide compatibility for assembly of components into a prosthetic socket. Modularity also generally refers aspects of assembling a prosthetic socket, wherein modularity provides variation in dimensions or shape from parts that are interchangeable within the specific component types. The interchangeability aspect of modularity also relates to repair, or reconfiguration of an assembled device, simply by switching components in and out. Accordingly, embodiments of the assembled sock can vary in dimensions and shape, and further are accompanied by these capabilities of repair and reconfiguration.

Some embodiments of the invention relate to a direct-fitting method of selecting and manipulating component parts such that the assembled socket substantially fits the residual limb of the person who has had the amputation, and who will be wearing the socket. Direct fitting is a term of art that is generally understood as excluding the use of molds in a fitting process. Casting of physical forms and the use of molds to replicate forms or create complementary forms relate to the use of intervening physical forms to transfer information about dimension and shape. Direct fitting involves methods that transfer measurements or maps of dimension and shape directly to the fabrication of replicate objects or complementary objects, such as a socket that is complementary to a residual limb.

Some embodiments of the invention may include an aspect of fitting that relates to more than simple fitting with regard to a static version of size and shape. Embodiments of the invention take into consideration aspects of the movement and physical activity that are particular to the individual, as may be habits of the person. Some body movements may relate to types of daily activity that the individual engages in habitually, or wishes to continue to engage in. These considerations relate to direct fitting that is biomechanically appropriate for the individual. By way of a simple example, the residual limb of an athlete, a sedentary person, or an elderly person, may all be very similar in size and shape, and yet the biomechanics associated with these respective residual limbs can be very different. Direct fitting, in this context and merely by way of example, may thus include measurements of dimension and shape of the residual limb through a range of motion, or under conditions of bearing weight, or in situations where the body of the individual is in varied positions. Aspects of such fitting may further include considerations of biological structure underlying the superficial aspects of dimension and form. By way of example, the biomechanics of soft tissue, or injured tissue, or bone and cartilage are different, particularly with regard to the ways in which these tissues respond to pressure, as may be imparted by embodiments of the prosthetic socket on the residual limb. These various considerations in the context of direct fitting may be referred to as dynamic fitting, or biomechanically appropriate fitting.

Some embodiments of the invention may include adjustability of dimensions or shape and contours of the prosthetic socket. Adjustability is advantageous in several aspects. For example, the residual limb is a living structure that can change in dimension or shape over time. Such changes can occur even in short periods of time, such as during a day, or according to the physical position of the individual, or whether the individual is walking or sleeping. In another time-related example, if the individual to be wearing the prosthetic socket is still a growing child or adolescent, the dimensions, shape, and biomechanical demands will definitely be changing. Similarly, of course, dimensions, shape, and biomechanical considerations change as an individual may be physically declining with age or due to health issues. Adjustability can accommodate such changes.

In another example, dimensions or shape or biomechanical demands can change according to the activity of the person. Further still, the subjective sense of what is comfortable for the person may change, even in the absence of physical change in dimension or form. Accordingly, capabilities and mechanisms of adjustment are attributes of some embodiments of the prosthetic socket. Such adjustability may include the dimensions or shape of the prosthetic as a whole, potentially involving more than one component of the socket. And in some embodiments, adjustability may relate more particularly to adjustability features of particular components, which, in turn, manifest as adjustable aspects of the prosthetic socket as a whole.

Turning now to embodiments to summarize in further detail, one particular embodiment relates to a modular prosthetic system that includes a prosthetic socket for a residual limb of an individual person, the residual limb having individual dimensions and anatomical contours, the prosthetic socket having dimensions and contours that substantially fit the dimensions and contours of the residual limb, the prosthetic socket including an assembly of components from each of three groups of socket components. These groups of socket components include (a) one or more struts arranged longitudinally with respect to the residual limb, each strut having a distal end and a proximal end, (b) one or more proximal brim members arranged proximally with respect to the one or more struts and connected directly or indirectly thereto, and (c) one or more distal socket members disposed at the distal base of the prosthetic socket. One or more of these socket component groups include modular components, the modular components having (1) variation with respect to dimensions and/or contours and (2) common connecting features that permit assembly of the components from the three groups of components together to form the prosthetic socket.

While these three particular groups of components are recited as examples of the invention, the scope of the invention includes other components, and any prosthetic socket component, including any particular component or accessory element associated with the prosthetic socket that can be modular in the sense that is described herein. And, particularly included within the scope of this invention is any prosthetic socket member, or component, or associated apparatus that is described or depicted herein.

Detailed aspects of this first particular embodiment will be elaborated on below. Following that, other embodiments will be summarized as alternative embodiments that may also include all of the features summarized in the context of the first embodiment.

In some embodiments of the invention, when the individual person for whom the prosthetic socket is intended engages or desires to engage in a range of daily activities, the dimensions and contours of the socket may be further selected, configured, or modified so as to be biomechanically appropriate in the context of the daily activities of the person.

Whereas the embodiment above is summarized as having one or more of the groups of the three groups components including components that are modular in nature, in other embodiments, either two of the three groups, or all of the three groups may be modular in nature. Modular, in this context, refers to having common attachment or connecting features despite having variation in dimension or shape. These variable aspects with regard to dimension or shape may be selected either on the basis of fitting the dimension and shape of the residual limb, or on aspects of the dimension and shape of the residual limb as the limb may assume when in motion or generally engaging in biomechanical dynamics associated with activities of daily living.

Some embodiments of a prosthetic socket system may include an inventory of components for each of the groups of components that are modular; the components that are selected for contributing to the assembly of a finished prosthetic socket may be selected from such inventories. As recited elsewhere, embodiments of the prosthetic socket system may include further components or accessory mechanisms that, like the three particular groups of components recited, are also modular. Accordingly, such other modular components participate in the invention by way of being deliverable from inventories of such components. Any component included in the assembly of a prosthetic socket, as provided herein, is included in the scope of the invention, particularly any component that is directly associated or interactive with any of the three particular groups of components recited. Further particularly included is any component or any member of a prosthetic socket that is described or depicted herein.

Typically, the components selected from an inventory of components for assembly into the prosthetic socket are selected by a direct fit approach. The criteria for selecting by a direct fit approach are to optimize the fit of the assembled prosthetic sock with respect to the dimensions and contoured aspects of the residual limb, and the criteria may further include optimization of the biomechanical appropriateness of the assembled prosthetic socket.

Inventories, as embodied by the invention, may include collections or kits of immediately available components, or the inventory may have on-demand nature, such that when a desired component is not immediately available, it can nevertheless be ordered or fabricated, as needed.

In various embodiments of the prosthetic socket system, the modular components from any of the three groups of modular components, as may be provided by inventories, may be any of a prefabricated component having various attributes regarding the nature of their from, whether its fixed or changeable. Accordingly, prefabricated prosthetic socket components may be any of, or any combination of standardized or substantially fixed form, a custom-fabricated or custom-molded component, a malleable or mechanically reformable or modifiable component, a component having an adjustable aspect of dimension or contour, or a component having a phase-changing composition that provides alternative dimensions, shape, or material propertied according to phase.

Some of these recited types of prefabricated components may be modified before being included in the assembly of a prosthetic socket. With regard to any aspect of dimension or shape, of any of the modular components that is modified so as to fit the dimensions or shape of the components of the residual limb, such modification may occur by way of a direct fit process.

As recited elsewhere, the scope of the invention as it relates to these various fixed form vs. changeable form attributes of components used in the assembly of a prosthetic socket include components beyond the three particular examples of modular components described and depicted herein. Further, while these attributes of components are being related here in terms of their assembly, such attributes also relate to repair and reconfiguration. Further, while changes in dimension or shape are being related in the context of component changes prior to assembly of the socket, at least some of such changeable aspects of shape or dimension that may occur after assembly of the components into the full prosthetic socket.

In various embodiments of the prosthetic socket system, as just referenced, various dimensions or contours of the prosthetic socket may be adjustable. With regard to dimensions, for example, any of length, width, circumference, or volume may be adjustable. With regard to shape, any aspect of shape may be adjusted, such as contours or angulations, merely by way of example.

In various embodiments of the prosthetic socket system the adjustable dimensions or contours of the prosthetic socket may occur by way of mechanisms or approaches that affect the dimensions or shape of the assembled prosthetic socket as a whole. In other embodiments, the adjustability of dimension or shape of the prosthetic socket occurs by way of adjustment or adjustments made particularly to any one or more of the components as selected from the groups of modular socket components.

In various embodiments of the prosthetic socket or the modular components thereof, adjustability can be performed either by a person, such as a prosthetist, or such the individual person for whom the prosthetic socket is intended. Adjustments may be made to the prosthetic socket while the socket is being worn, or when it is removed and more easily manipulated. In other embodiments, adjustability may occur automatically, or with mechanical assistance. In some embodiments, the prosthetic socket includes a microprocessor in operable association with an adjustability mechanism; in these embodiments the adjustable dimensions or contours of the prosthetic socket may be operably adjustable by the microprocessor and associated mechanism.

The prosthetic socket may be understood to provide a volume in which the residual limb is accommodated. The volume is encompassed within a circumferential area internal to the struts, a distal boundary according to the distal base of the socket, and a proximal boundary according to the proximal ends of the struts. In some embodiments of the prosthetic socket, such volume may adjustable, either by adjusting dimensions, shape, or a combination thereof.

In some embodiments of the prosthetic system, a prosthetic socket component comprises a moldable composition that may be adjusted or reformed. In typical embodiments that are adjusted or reformed, such changes may be made by a method comprising direct molding of the component against at least a portion of the residual limb. Merely by way of example, such component may be moldable by way of heat sensitive lability or by curing, in order to stabilize the molded form.

As referenced above, embodiments of the prosthetic socket may be sized, shaped, or adjusted so as to be biomechanically appropriate both for the residual limb, itself, but more generally for the activities of the person, or for particular aspects of anatomy and tissue that underlie the superficial aspects of residual limb dimension or shape. In some embodiments of the prosthetic socket, biomechanical considerations particularly concern the distribution of pressure against the residual limb in a controlled manner when the prosthetic socket is being worn by the individual Accordingly, in some embodiments the pressure from the prosthetic socket on the limb may be distributed with substantial evenness across an interfacing region between the prosthetic socket and a portion of the residual limb, when the residual limb is disposed within the socket. In other embodiments, the pressure from the prosthetic socket on the limb may be distributed preferentially toward one or more particular locales within an interfacing region between the prosthetic socket and a portion of the residual limb, when the residual limb is disposed within the socket. In any of these embodiments that relate to distribution of pressure by the socket against the residual limb in a controlled and biomechanically appropriate manner, a pressure distribution profile may advantageously take into account the range of activities of daily living.

Some embodiments of the prosthetic socket further include a flexible liner arranged to be internal to arranged to line an interior aspect of the socket, such interior aspect including interior aspects of any of the prosthetic sockets structural weight bearing components, as for example proximal brim member, the struts, or the distal members. When the prosthetic socket is worn by the person, the liner thus represents a surface across which pressure is mutually transferred between the prosthetic socket and the residual limb. In a typical instance and in the absence of an intervening liner, the structural weight bearing components provide the initial locus of pressure impinging on the residual limb from the prosthetic socket. In some embodiments, the flexible liner possesses sufficient stiffness and resilience that it can support distribution of at least some pressure across its surface, away from the struts or other structural weight bearing components. In some of these embodiments, the flexible liner has sufficient stiffness and resilience that it can support distribution of pressure with substantial uniformity across its surface.

Some embodiments of the prosthetic socket include an external weight bearing surface, the external surface comprising external aspects of any of the proximal brim member, the struts, or the distal member. In particular embodiments, the external weight-bearing surface has sufficient stiffness and resilience that it can support distribution of at least some pressure across its surface, away from the structural weight bearing components. In some of these embodiments, the external weight-bearing surface has sufficient stiffness and resilience that it can support distribution of pressure with substantial uniformity across its surface.

In some embodiments of the prosthetic socket, the one or more distal socket members disposed at the distal base of the prosthetic socket include a socket cup disposed within the distal base, the socket cup configured to support a distal end of the residual limb. As with other distal members or elements of the prosthetic socket, the distal cup may be modular in every sense of modularity recited elsewhere.

With regard to embodiments of prosthetic socket and its applicability and positioning on a residual limb when the socket is being worn by the individual person, a distal end of the amputated limb is supported by a distal socket member, a distal portion of the residual limb is supported by or within the one or more struts, and the portion of the residual limb proximal to the portion embraced or supported by the struts is supportably enclasped by the proximal brim.

Embodiments of the prosthetic socket are adaptable to a residual post-amputation portion of any of both an upper extremity or a lower extremity. With regard to an upper extremity, a residual post-amputation portion of the upper extremity may be at an above-elbow arm (trans humeral) site or a below-elbow (trans-radial) arm site. With regard to a lower extremity, a residual post-amputation portion of the lower extremity may be at an above-knee (trans-femoral) leg site or a below-knee (trans-tibial) leg site. Basically, embodiments of the prosthetic device may be adaptable to any conventional site of amputation, at any level. Further, embodiments of the prosthetic device may be adaptable for use as any of an immediate post-operative socket, a diagnostic socket, a temporary socket, or a definitive socket.

In various embodiments of the prosthetic socket, components from any of the three recited groups of socket components (distal members, struts, proximal brim members), and any other component of the prosthetic socket may include a shock-absorbing material. By way of example, one particular material is low durometer silicone.

A common problem for prosthetic sockets, in general, relates to the accumulation of moisture that originates from the surface of the residual limb. Such moisture can be irritating or uncomfortable to the wearer of the socket, or worse, it can contribute to sores, and it may generally compromise functionality of the prosthetic system. Accordingly, some embodiments of the prosthetic socket may include a moisture management or evacuation system. Aspects of a moisture evacuation system may be included in any portion or any component of the prosthetic socket, including, in particular components from any of the three recited groups of components (distal member, struts, proximal brim members).

Examples of moisture evacuation systems included in the scope of the invention include any one or more of a roll-on gel liner with integrated vertical moisture wicking channels, proximal internal and external seals, moisture expulsion valves, and a locking mechanism with an integrated moisture evacuation route.

As recited above, embodiments of the prosthetic socket may have a single strut, however other embodiments include a plurality of struts such as two or three, or more. Some particular embodiments include four struts. Struts, if plural, are typically arranged circumferentially around a central space that the residual limb occupies when the individual is wearing the prosthetic socket. Embodiments of the invention include any practical or biomechanically advantageous spatial arrangement of the struts. In some embodiments, the struts are evenly spaced apart. In some embodiments, the struts are arranged in a symmetrical manner, and in some embodiments, struts are arranged in an overlapping manner.

The distal ends of the struts are typically arranged to support distal members of elements of the prosthetic socket. In some embodiments, the struts are mutually convergent at their distal ends, and joined to form a distal base of the prosthetic socket. In other embodiments, the struts do not converge themselves, but they support a distal base including one or elements, such as a distal cup.

The surfaces of strut embodiments can interface directly with the residual limb, although in some embodiments flexible liners may be disposed within internal aspect of the socket, thereby intervening between the struts and the residual limb. By any arrangement, however, it is advantageous for the struts to present tissue-friendly, non-irritating or non-injurious, or biomechanically appropriate surface that will abut residual limb tissue when the socket is being worn. Accordingly, and merely by way of example, struts may include any one or more of an oval-shaped cross section, rounded edges, or a surface that is convex with respect to the residual limb surface.

In some embodiments of the prosthetic socket system, any one or more the modular prosthetic socket components may include features that provide adjustability to dimensions or shape, such as, merely by way of example, in any of length, height, width, curvature, contoured aspects, conformability, flexibility, rigidity, durometer, elastic modulus, positional orientation, and angulation.

In some embodiments, adjustability is provided by a mechanical apparatus or arrangement of interacting elements. One particular mechanical arrangement may include a telescoping mechanism that can affect strut length or width. In some embodiments, adjustability mechanisms may include gearing features, cam elements, or moveable wedges.

Some embodiments of the prosthetic system may include one or more encircling bands around the struts or around the brim members, as summarized further elsewhere. These encircling bands can provide a relatively static support roll, in which they stabilize or secure the struts or any structural component, contributing to the overall structural integrity of the prosthetic socket, or they provide a more active adjustable role. Adjustments provided by an encircling band may include adjustments to the circumference of the socket, or more particularly to the circumference described by the struts. Alternatively, inasmuch as the encircling bands can be elastic or tensionable, the encircling bands can adjust tension imparted to the struts even in the absence of noticeable change in circumference.

In various embodiments of the prosthetic socket, one or more of the adjustable aspects of any structural component may manually operable, such operability available either to the person wearing the prosthetic socket or to a prosthetist working with the person. Adjustments may be made either when the prosthetic socket is being worn, or when it is not being worn by the person.

In other embodiments of the prosthetic socket, one or more of the adjustable aspects of any structural component may be automatically operable. Automatic, in this context, refers to the participation or facilitation of adjustment by any non-manual approach, including adjustments facilitated by microprocessors, or by material properties that confer adjustability. Accordingly, some strut embodiments are operably adjustable by a microprocessor and an associated adjustment mechanism.

In other embodiments, a strut may be adjustable by changes that occur in phase change materials incorporated in the strut. Merely by way of example, phase change properties may elate to any one or more of durometer, rigidity or elasticity, electrically catalysable changes, light activatable changes, chemically-catalysable changes, or temperature-related changes.

As noted above, some embodiments of a prosthetic socket may include one or more encircling bands arranged around and connected to any prosthetic socket component, as for example, the struts or proximal brim members. In some embodiments, an encircling band is arranged and adapted so as to apply pressure radially inward on the struts. In some embodiments, the circumference or tension of an encircling band is adjustable. In various of these embodiments, an adjustment of the circumference or tension of the encircling band is operable to adjust a shape or contour of the prosthetic socket.

Some embodiments of the prosthetic socket the socket include two or more encircling bands arranged around and connected to the longitudinal struts, and the socket includes at least one tensioning band connecting the at least two encircling bands, as for example, in an interlaced manner. In such embodiments, the two or more bands may be arranged in a longitudinally spaced apart relationship, and the interlaced tension bands may be arranged to stabilize that spaced apart relationship. Further, in some embodiments that include tensioning bands associated with either the struts or the encircling bands, tension bands are adjustable such that the tension they provide is adjustable.

Some embodiments of the modular prosthetic system, in addition to the prosthetic socket as extensively described herein, may further include a distal operable prosthetic element connected to the distal base of the prosthetic socket. Such operable prosthetic element may be of any type known in the art, such as wherein any of a prosthetic elbow, a prosthetic hand, a prosthetic knee, or a prosthetic foot.

Some embodiments of the modular prosthetic system, in addition to the prosthetic socket itself, may further include a suspension mechanism or rigging for the socket that is configured and arranged to support maintenance of the prosthetic device on the residual limb. Embodiments of the suspension system may be generally of any conventional type known in the art. The suspension systems may also be understood as modular in nature, in that in spite of variations in form or structure, they include attachment features that have substantial commonality or sufficiently flexibility that they can be operably attached to the prosthetic socket.

In some prosthetic system embodiments that particularly include a suspension rigging or mechanism, the system includes an inventory of such mechanisms or riggings, from which an embodiment appropriate for the individual may be selected. As with other modular aspects of the prosthetic system, modular suspension mechanism variations can include variations in dimensions and aspects of shape or configuration, but include attachment features in common that attach to compatible attachment features of the prosthetic socket. The suspension mechanism variations in the inventory may be selected for structural features that fit the person and are biomechanically appropriate for activities or desired activities of the person.

Embodiments of the prosthetic socket may further include other components or members, such as, and merely by way of examples, an ischial weight-bearing member, a tendon-wearing member, a supercondular extension member, a support or control extension member, a proximal brim member adapted for ischial weight-bearing, or a proximal brim member that is specially designed for pattelar tendon weight-bearing. Any of the members may have modular aspects, and may be drawn from an inventory of such components, as has been described in the context of other modular components provided herein.

Some embodiments of the prosthetic system, the prosthetic sock, or any particular component thereof may include sensors. Typically, such sensors are in an operable relationship with either a microprocessor and/or responsive mechanical elements. Such sensors may include, merely by way of example, an accelerometer, an inclinometer, or a gyroscope. These sensors and associated smart, operable, or responsive components may be understood to provide adjustability to the prosthetic socket. In some embodiments, the microprocessor is in communication with one or more additional and separately located sensor or microprocessor, said additional and separately located sensor or microprocessor may be disposed in any appropriate location within the prosthetic socket, or at another location within a larger prosthetic device that also includes the prosthetic socket.

As with adjustability as described elsewhere herein, adjustability is generally directed toward optimizing aspects of fit and flexibility, and aspects of biomechanical appropriateness for the individual. These forms of adjustment would generally be considered automatic by virtue of microprocessors and responsive mechanisms, but they may also include manually operable options.

In addition to the first embodiment of a modular prosthetic system, as referenced above and then extensively detailed, the invention includes other particular embodiments. In the first embodiment, the prosthetic socket is one in which at least one of the three recited groups of components (struts, proximal brim members, and distal socket members) include components that are modular in nature. In the first embodiment, the prosthetic socket had dimensions and contours that substantially fit the dimensions and contours of the residual limb.

In a first alternative embodiment of a modular prosthetic system, all of the three recited groups of components are modular. And the this first alternative embodiment, the prosthetic socket, in addition to the prosthetic socket fitting the dimensions and contours of the residual limb, the prosthetic socket is further configured to biomechanically appropriate for a range of activities in which the individual engages in, or in which the individual desires to engage, or desires to continue to engage in.

In a second alternative embodiment of a modular prosthetic system, with reference to the three recited groups of components, all of the three recited groups of components are modular, and at least one of those three groups of modular components includes components that are adjustable with respect to component dimensions of contours.

In a third alternative embodiment of a modular prosthetic system, with regard to the three recited groups of components, all three of the recited groups of components are modular, and the system further includes an inventory of modular components for each of the three groups of modular socket components. Modular components from each of the groups selectable for assembly into a complete prosthetic socket.

A fourth alternative embodiment of the invention provides a kit of components from which a modular socket may be assembled. All of the recited groups of socket components are modular, and the components from the groups of socket components included in the kit are selected so as to be assemblable into a prosthetic socket that substantially fits the dimensions and contours of the residual limb and is biomechanically appropriate for activities of the individual.

Embodiments of the invention also include methods of making or assembling a prosthetic socket for a residual limb of an individual person who has experienced the amputation of an extremity. Accordingly, one particular method embodiment is directed to making a modular prosthetic socket fitted to a residual limb of an individual person, the residual limb having individual dimensions and anatomical contours.

This method embodiment includes providing inventories of one or more groups of modular prosthetic socket components from which to assemble the prosthetic socket, the components within each group having (1) variation in dimension or contour and (2) common connecting features that permit assembly of the individual components together to form the prosthetic socket. This method embodiment further includes, with reference to the inventory of each component group, selecting one or more components therefrom to assemble a residual limb socket that will substantially fit the individual dimensions and contours of the residual limb when said components are later assembled into a residual socket. And the method further includes assembling the selected prosthetic socket components from each of the groups of components to form the prosthetic socket for the residual limb.

In this method embodiment, the groups of prosthetic components for which inventories are provided include (a) struts to be arranged longitudinally with respect to the residual limb, each strut having a distal end and a proximal end, (b) proximal brim members to be arranged proximally with respect to the one or more struts and connected directly or indirectly thereto, and (c) distal socket members to be disposed at the distal base of the prosthetic socket. In method embodiments wherein the three groups of prosthetic group components are modular in nature, the method may further include selecting components from all three groups and assembling them together to form the socket.

While these three particular groups of components are recited as examples that are involved in the method, the scope of the method includes the use of other components, and any prosthetic socket component, including any particular component or accessory element associated with the prosthetic socket that can be modular in the sense that is described herein. And, particularly included within the scope for use in the method is any prosthetic socket member, or component, or associated apparatus that is described or depicted herein.

In some embodiments of the method, selecting a prosthetic socket component is based on determining aspects of dimension and/or contours of the distal portion of the residual limb, said determining step including any one or more of scanning, photographing, casting, or mapping with a three-dimensional point reference device a three-dimensional digital or physical representation of the residual limb.

In some embodiments of the method, selecting individual prosthetic device components includes directly fitting the components to achieve the dimensions and anatomical contours of the assembled socket. In some embodiments of the method, selecting individual prosthetic device components may includes directly fitting the components to achieve a fit that is biomechanically appropriate for activities of the person. A fit that is biomechanically appropriate may include taking into consideration the height and weight of the person, and it may include taking into consideration distribution of pressure by the prosthetic socket on the residual limb.

In some embodiments of the method, a component selected from an inventory of group components includes a composition that is moldable; in this case, method may further include molding the component directly against at least a portion of the residual limb. Such molding is typically performed in order to improve the fit of the prosthetic socket with regard to the dimensions or contours of the residual limb.

In some of the component embodiments, the moldable composition is labile to heat at a temperature that is sufficiently low so as to not injure a residual limb when the limb is protected by a thermal barrier. In this case, the method may further include heating the moldable component, thermally protecting the residual limb with a flexible thermal barrier, and molding at least a portion of the component against the portion of the residual limb. In some of the component embodiments, the moldable composition is a curable composition. In this case, the method may further include molding the component against at least a portion of the residual limb, and then curing the component in its molded form.

In some embodiments of the method, prior to the assembling step, the method includes providing an inventory of encircling members that are configured to be arranged orthogonal to the struts and connected thereto, and then including the encircling members in the assembling step.

Some embodiments of the method further include adjusting any of the dimensions or contours of the prosthetic socket. In some of these embodiments, adjusting any of the dimensions or contours of the prosthetic socket includes improving the fit of the socket to the residual limb. In some embodiments of the method, adjusting any of the dimensions or contours of the prosthetic socket may further include improving a biomechanically appropriateness of the dimensions or contours for activities of the individual.

In some embodiments of the method, the adjusting step is performed by a professional prosthetic fitting expert. In some embodiments, the adjusting step may be performed by the person wearing the socket. In some embodiments, the adjusting step is performed automatically by a microprocessor-associated mechanism.

In some embodiments of the method, adjusting any of the shape or dimensions of the residual limb socket frame may include adjusting a volume encompassed within a circumferential boundary defined by the struts, a distal boundary according to the distal cup, and a proximal boundary according to the proximal ends of the struts.

In some embodiments of the method, adjusting may include redistributing pressure exerted by the prosthetic socket on regions of the residual limb, such redistribution referring to when the person is wearing the prosthetic socket.

BRIEF DESCRIPTION OF THE DRAWINGS

FIG. 1 is a perspective view of an example of a right above-knee (trans-femoral) prosthetic socket after the modular members have been selected, assembled, formed, and adjusted to fit over an individual's residual limb.

FIG. 2 is a perspective view of an example of a right above-knee (trans-femoral) prosthetic socket after the modular members have been selected, assembled, molded, but before it has been directly molded and adjusted to fit over an individual's residual limb.

DETAILED DESCRIPTION OF PREFERRED EMBODIMENTS

Overview

Figure 3:
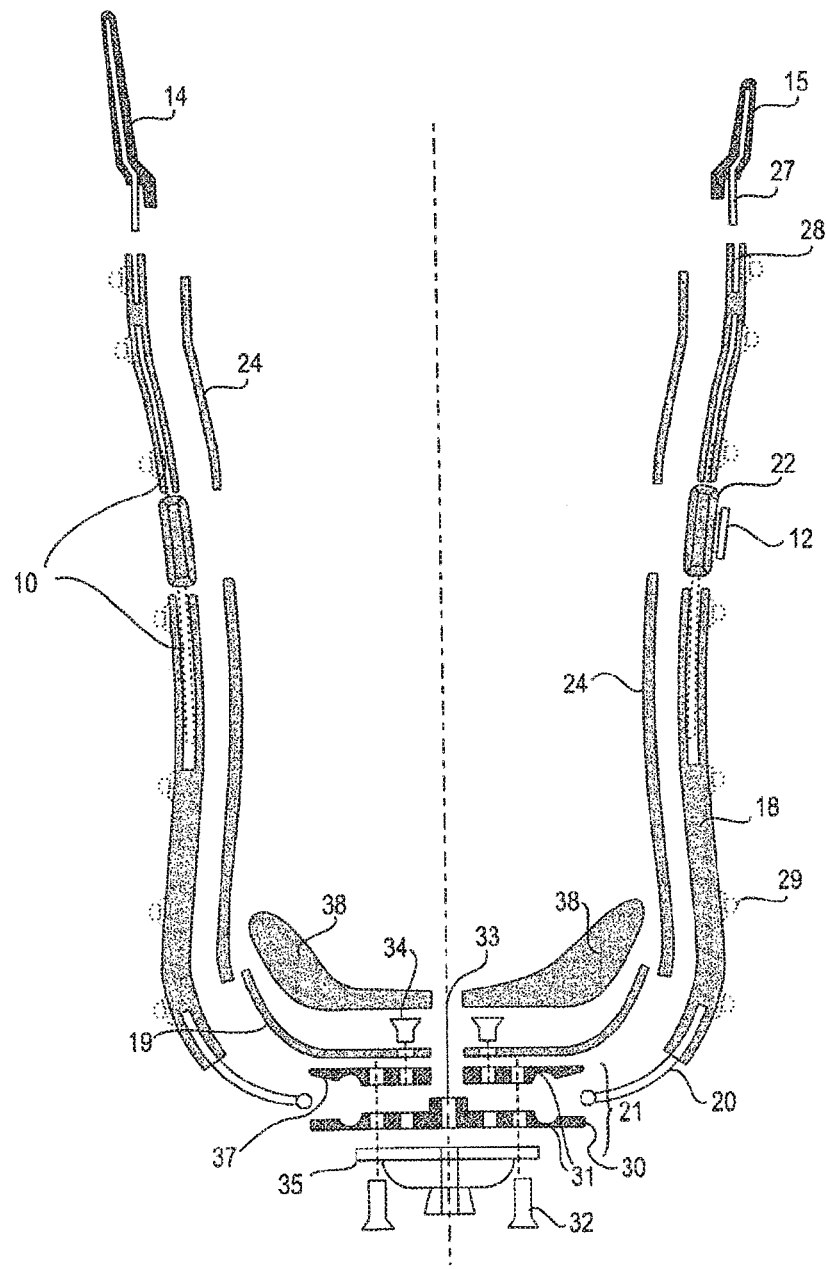
FIG. 3 is a frontal cross sectional view of an exploded right above-knee (trans-femoral) prosthetic socket.

The applicability of molds to the process of creating sockets that accommodate residual limbs and to provide a proximal base for effective prosthetic limbs and operable distal effectors is pervasive in the prior art, and has also been broadly helpful and therapeutically beneficial. As presented in the background, however, there are inherent and practical limitations to this approach. Such limitations relate to resources, such as time and cost, and to actualities of fit to a residual limb, wherein fit relates to a limb portion that is actually not well suited for bearing weight, providing a base of prosthetic limb operability. A residual limb comes with complications related to body heat and moisture that effect the interaction of the residual limb and the socket. And, the residual limb, itself, is dynamic in shape and internal structural details over time. These changes occur both in the short term, as during the course of a day, and in the long term, as the individual ages and deals with changes in body structure and activities of daily living.

A number of innovations disclosed herein address these briefly described complicating aspects of providing a residual limb prosthetic socket to that fits well, as a baseline, but is further dynamic in aspects of its fit, and adjustable in aspects of its fit. As may be understood by this disclosure, these aspects of fit, dynamicity of fit, and adjustability of fit, at least in part, relate to the direct-fit manner in which embodiments of the invention are made.

Embodiments of a method for making a prosthetic socket, as described herein, may use a plurality of premade or custom-made members that are designed to function in a compatible way with one another, and are individually selected and assembled in a customized and specific manner to form a modular prosthetic socket to meet the needs of any amputee, whether for an upper or lower extremity.

Embodiments of residual limb sockets described herein may include a distal base member with specialized and contoured pressure distribution struts. In one embodiment, by way of example, two flexible and adjustable members are positioned within each of the vertical and rigid strut sections (vertical strut sections comprise the two flexible sections and two rigid and specially contoured strut members made of carbon fiber and/or acrylic resin). An adjustable proximal brim with a ratcheting patient-operated control may be used. The specialized contours of the present prosthetic socket are configured to block rotation, and to provide control and stability inside the socket with comfort and without the need for total contact. This arrangement provides the advantage of greater heat dissipation and a non-circumferential design that allows greater adjustability. Other embodiments, however, may include a liner that provides total contact between the socket surfaces and the residual limb.

The present invention allows for various types of sockets and various options for pressure profile distribution, as well as the modular and adjustable ability to change as the patient changes.

Embodiments of the basic method for making a prosthetic socket described herein include a modular approach that uses a plurality of pre-fabricated or custom-made members that are individually selected, oriented, and assembled in a customized and specific manner to meet the needs of the amputee. The result of this modular prosthetic socket method is a custom modular member prosthetic socket. The custom modular member prosthetic socket allows for one trained in the field to fit the prosthetic socket directly to the amputee's residual limb for an amputee of either the upper or lower extremity, without the need to make a negative mold or a positive mold. The custom prosthetic socket can achieve optimal functioning results and comfortable fit by applying pressure in pressure tolerant areas of the residual limb, while simultaneously relieving pressure in pressure sensitive areas of the residual limb. A total surface-bearing interface may augment the modular support frame of the custom modular member prosthetic socket for those who require a circumferential or total surface-bearing prosthetic socket. Once fit to the amputee's residual limb, the modular system can serve as a complete, independent, and fully functioning prosthetic socket with its own interface options. Alternatively, it can be made to work with other related devices, including gel liners, suction systems, pin systems, vacuum systems, adjustable systems, and modular alignment systems.

Each member for the modular method is designed for compatible assembly. The modular method may include adjustability or conformability within one or more of its members. This adjustability may come in the form of being able to be trimmed to the proper size, heat molded, formed to shape, and then set. The adjustability includes telescoping height adjustability, hydraulic controlled adjustability, pneumatic controlled adjustability, hinged controlled adjustability, slide controlled adjustability, foldable adjustability, and ratcheting adjustability. The members of the socket are thus expandable, or otherwise mobile, conformable, changeable, or adjustable. By selecting individual members and adjustability of individual members, then orienting and assembling selected members to match the needs and conditions of the amputee, the modular methods and resulting products described herein offer the advantages of a custom made prosthetic socket with design modularity, while at the same time avoiding time consuming and wasteful mold making techniques as well as the disadvantages and limitations of premade sockets and alternative approaches of the prior art.

Embodiments and Features

The specific members, orientation, adjustability, materials, shape, contour, and relationship of embodiments of the modular prosthetic socket described herein are diverse in some aspects of their form, but nevertheless have features in common, particularly connection features as befitting of a modular overall design. Modularity is purposefully directed toward providing versatility and adaptability. The design is such that each member can be selected for its material composition, strength, durability, cost, shape, and size to match the needs of a particular amputee. Further, the relationship between and among members, including their adjustability properties, locking abilities, control method, fastening method, and orientation, may also be selected to match the needs of the patient. A pre-fabricated hinge and/or control mechanism may be selected if an adjustable and locking relationship is desired. Since the size, shape, and needs of all residual limbs are unique to each specific individual, each produced embodiment or rendering of the methods of making and using embodiments may be any of individualized, or custom-made, custom-assembled, or custom-adjusted. For the sake of describing the invention in detail, as a general module, as templates, as standard sizes or forms, as an inventory, as a kit, and as particular embodiments are described. In general, the modular prosthetic socket method described may include one or more of the following types of pre-fabricated or custom-made members: a distal control and attachment member, one or more adjustable members, one or more structural struts or longitudinal links, height or length adjustable or extendable members, and/or width adjustable or extendable members, proximal brim and/or connecting link members, and additional members.

The modular members, per embodiments of the invention, may be made in a series of sizes and shapes of premade members that may be selected to fit a substantial portion of the residual limbs extant within the population people with amputations. For cases where the shape, contour, or size of the amputee does not work well with premade members, custom molded members may be fabricated independently of or in conjunction with members that may be provided in a range of standardized sizes or form, as for example, could be included in an inventory of parts. The custom molded members may be made with pre-made members that are made with a moldable material, or they may be made with one of the techniques that are already available in commerce.

Embodiments of the invention also are adjustable, such adjustability provided, at least in part, by a modular approach to assembly. Adjustability and modularity lend themselves particularly well to trial fittings and trial periods of use, in order to arrive a final version of a residual limb socket and related prosthetic components. Trial fittings and trial periods of use also may be appropriate as needs of the patient change, or as the physical from of the residual limb changes over time.

The distal member of the modular socket design, as provided herein includes attachment and adjustability mechanisms that are appropriate and compatible with modular alignment and component connecting members. This connection mechanism of the distal member serves as a connector between the custom member modular socket and an adjustable or non-adjustable pylon, modular alignment system, or other component connection like a knee, foot, or hand. The connection member is designed for ease of use and compatibility with previously established modular alignment devices, as well as a wide array of alignment options to work properly with the different alignment needs of different individuals.

Typical applications for embodiments of the modular method and device product include any of a definitive prosthetic socket, a temporary prosthetic socket, an initial prosthetic socket, a post-operative prosthetic socket, and a diagnostic prosthetic socket.

Customizability by Way of a Modular Assembly

Embodiments of the invention provide a modular prosthetic socket method and resultant product where pre-fabricated or custom made modular members are selected and linked together to fit the needs, shape, and size of any amputee's residual limb, for either the upper and lower extremity. The modular and adjustable prosthetic system or parts therein may be used as any of a definitive prosthetic socket, temporary prosthetic socket, initial prosthetic socket, post-operative prosthetic socket, diagnostic prosthetic socket, and/or as a casting aid for a prosthetic socket. The modular method and resultant product comprises prefabricated or custom members, and may include any of the following: distal control and attachment member, one or more adjustable members, one or more structural struts or longitudinal links, height or length adjustable or extendable members and/or width adjustable or extendable members, proximal brim and/or connecting link members, and additional members.

A variation in the fitting process of the modular design may include having a plurality of members that are preassembled for standard sizes, but allow for customized adjustment or swapping out of members to individually fit a given amputee. Hence, standard or typical limb sizes and shapes may be pre-assembled or partially pre-assembled, and then simply custom adjusted or modified to match the individual. An advantage of this approach is that less time is required to fit standard or common residual limb sizes and shapes. This alternative fitting method still provides the advantages of the modularity in design, in that it offers such benefits as augmentation and adjustability.

The embodiments of the methods, resulting products, and designs described herein may be applied to other applications that are related to prosthetic devices, such as orthotics, robotics, crutches, exoskeletal applications, wheelchairs, mobility equipment, and other applications.

Embodiments and Features of a Distal Cup

The distal control and attachment member embodiments may be a custom made or a pre-fabricated contoured distal "cup". The distal cup may vary for different amputation levels and sizes of the residual limb, and may be a fixed form or moldable or adjustable by heat modification or other method to reshape or accommodate for any high-pressure areas, sensitive areas, or otherwise specific areas. This process of adjustability may vary or differ per application. It may include use of materials such as heat relievable thermoset plastics and thermoplastics. The distal cup may also be made of a moldable material such as carbon or fiberglass braid with water-catalyzed resin, UV catalyzed resin, or other suitable material. Designs may vary, depending on the specific application, circumstance, and location of application. The variability of options for materials, sizes, and methods is designed to meet the size, amputation level, and functional needs of any amputee.

This distal section serves as an attachment segment where various types of components and additions may attach both proximally and distally. For example, there may be a compatible four hole attachment pattern and center bolt acceptor that can work with various and standard manufactured knees, feet, and other terminal devices. The distal cup may also have an integrated distal end pad that is either custom made or off-the-shelf, and/or suspension components such as a lanyard suspension system, suction suspension system, pull-bag suspension system, pull n' tie suspension system, or other suitable system. The distal cup also serves to control the distal aspect of the amputated bone. This is a key aspect to the design, in that an amputee must have adequate control of the prosthesis for successful use thereof. Moreover, distal control is critical to biomechanical control and stability. The distal cup is designed to serve in providing this control by having multiple contoured shapes that can work to provide anatomical control for the various levels of amputation. For example, trans-femoral amputees commonly get excess pressure and resultant pain at the distal lateral and distal posterior-lateral aspect of the prosthesis due to the biomechanical forces in that area during gait. Therefore, the distal cup for trans-femoral amputees is designed to have a contoured relief and more proximal control crossbar options that will help to avoid these common problems. Another key aspect to the design is that the distal cup is made to allow for attachment of the control struts at the appropriate location, angle, and height to allow for maximized control of boney anatomy and accommodation of soft tissue.

For a push-on suction socket variation, various sizes of pre-made distal suction cups made out of silicone, urethane, or other appropriate material can be fit to the patient, or if the patient does not fit well in the off-the-shelf sizes, a custom silicone distal suction cup may be fabricated. The selected material for the distal silicone cups may include design details such as softer durometer distal portions to improve comfort as well as adapting the contour to match the patient, and outside material distally to improve the ability to adhere to the distal base member. This silicone cup may have integrated locking/securing members that may then be locked into and adhered to the distal base of the modular cup. For example, Velcro type tabs can be integrated into the distal silicone cup, which can lock into the socket, or set screws, can be used as well as undercut tabs that allow the silicone cup to lock into place in the socket. To ensure an optimal fit between the silicone distal suction cup and the distal base member, silicone adhesive, silicone replicator, or other material may be used to adhere the silicone distal suction cup to the distal base member while at the same time filling in any voids or lack of total-contact. From the distal base with integrated distal suction cup, any of the modular member options may be selected as usual to match the patient's needs. This push-on suction socket style is especially applicable to disarticulation level amputees.

Embodiments and Features that Provide Adjustability

Embodiments of a prosthetic socket as provided herein may include one or more adjustable member, mechanical joints, hinges, flexible sections, durometer changeable sections, replaceable fixed angle sections, microprocessor controlled joints, and/or other suitable adjustable sections that may be dynamically or statically adjusted to fit the patient and meet his or her needs. This adjustable section is one way that the present invention allows for volume adjustability or changes to the amputee's residual limb. As presented, the mechanism of adjustability may vary. There may be a specialized hinge or adjustable section that may be automatically or manually adjusted to meet the amputee's needs. If automatically adjusted, the system may include the use of pressure sensors and a microprocessor or microprocessors that control adjustment of the socket automatically to avoid excess pressures. The mechanism of automated adjustment may be a geared mechanism, ladder ratcheting system, automated set pin, hydraulic control, pneumatic control, or other suitable system. A mechanically adjustable section may also be utilized where a manual set screw, button lock, bail lock, drop lock, ratchet lock, or other suitable manual set option may be utilized to set the angle of the adjustment or range of adjustments. The mechanical adjustable member may be manufactured as a specialty hinge, for example, that can easily be riveted to the distal control member and strut members, and may include a mechanism that allows for user or practitioner adjustability. The adjustable members can also be made to allow for installation into a lamination, and can also be made to affix and function with various socket materials.

A durometer or rigidity changeable sections may be utilized as an adjustable section member that has the ability to automatically or manually change in durometer at the desired time. For example, if the patient wants to adjust the fit of their prosthetic socket, he or she can pass a small electrical charge through their adjustable member section by pressing a button that then allows the specialized material to be flexible until at the adjusted position. Then it may be changed back to a stiff or set material. The adjustable member may also be a low profile and light option of a rigid plate that is selected for the correct angle, and may be wedged or changed out for a different angle for adjustment. If the weight or activity level of the amputee is such that the adjustable component requires reinforcement, such reinforcement may be added after the desired angle has been established by a riveted reinforcement beam, fiberglass tape, or other suitable way to increase the strength capabilities of the adjustable section. The manual or automated system may include or be integrated into the strut and distal cup design described above. For example, if a ladder and automated ratchet is utilized, the ladder aspect of the strut may be designed to slot into the shaft or long axis of the strut for which it controls. The advantage of such an integrated design is to protect components and reduce bulkiness of the overall design. The proximal brim design can also accommodate for the adjustability.

An addition to any of the embodiments described herein may be adjustable set screws, wedges, or other appropriate means to tighten and loosen the fit of the modular method socket onto the amputee's residual limb. The means of having such adjustability may vary in the ease of adjustability, cost, durability, and other properties. These means may therefore be selected or avoided altogether, based on the needs of the amputee, the environment, and cost constraints.

Embodiments that Provide Adjustability with Regard to Length

Embodiments of height or length adjustable or extendable members and/or width adjustable or extendable members may include of one or more expandable or adjustable members that may adjust or expand in height and/or width and may be added to, fastened to, or integrated with the strut section. The additions may be riveted in place, snapped on, manufactured as an integrated member within, or otherwise fastened in an appropriate way. This allows for increased variability to accommodate different lengths and sizes of the residual limb, and may be used in conjunction with the other adjustability and accommodative methods described herein. This adjustable aspect of the design may also be omitted if not required for certain amputees or for more simplified versions of the design.

Embodiments of Linking Elements

Embodiments of structural struts or longitudinal links may include structural weight bearing rigid or semi-rigid links or struts that may be selected and adjusted to match the amputee's needs. These links may be moldable or conformed for the patient by heat molding, resin curing, or other conformable options. The materials selected for these links may vary for the appropriate location and use of the prosthetic socket. For example, for developing country applications, locally available materials and interfaces, such as aluminum, fiberglass, bamboo, and locally available thermoset resins, may be selected.

Proximal Brim Embodiments

Embodiments of proximal brim members may include of one or more rigid, semi-rigid, and/or flexible members that attach to the struts. They may be adjustable or fixed dynamically or statically. For example, connecting links may include a ratcheting section that is patient adjustable, a fixed and contoured rigid section, a rigid and non-contoured section, and a flexible section. They may be designed to add support or control and/or allow for the full range of motion for the particular patient. They may also be utilized for suspension, such as a super condular proximal brim that suspends proximal to the condyles of the patient's skeletal anatomy. The proximal brim members of the modular and adjustable prosthetic system may be custom made for the individual or prefabricated. Prefabricated proximal brim sections are manufactured in such a way that they are sized, contoured, and adjustable in such a way that they can meet the needs of all or most amputees. This is accomplished by utilizing specialized members with contours and sizes that are appropriate for various sections of the socket and the various amputation levels. Such proximal brim members may be manufactured with various methods and materials that may vary per application and location. The members are designed to have specific shapes that work well to control movement of the prosthetic limb, while still being comfortable and allowing range of motion to facilitate the needs of different amputees. Such a proximal brim may also vary in its application and design as well as associated connection members and members that allow for adjustability of the proximal brim members depending on the needs of the patient. For example, the same proximal brim members may be selected for two different amputees, but the method of attaching them to associated members and adjustment pieces may vary. The base or default design will have a standardized proximal brim shape that is contoured to allow for muscle action and boney prominences that are typical for each amputation level with overlapping and adjustable segments that allow for adjustability that adapts to the patient's residual limb shape and size. An adjustable section may also involve a strapping or tying section and/or ladder and ratchet or other suitable system to allow for adjustability of the size of the brim design. The brim may include a moldable material that may be molded and remolded by heat, curable resin, or other suitable way to match the specific shape needs of the particular patient.

Additional Member Embodiments

Embodiments of a prosthetic socket, as provided herein, may include additional members such as, by way of example: ischial weight bearing seat extension members, tendon bearing extension members, supercondular extension members, support or control extension members, sensor members, levelometer members, accelerometer members, microprocessor members, automated or manual controlling members, padding or cushion members, lanyard suspension system members, pull-bag or pull-sock exit tubes suspension system members, pull-in sock or bag holding system for pull in and tie off suspension system members, suspension belt members, suction valve members, sealing sleeves or sealing system members, outside liner members, cosmetic and/or functional fairing members, sweat expulsion valve members, self alignable distal attachment member, open compatibility distal attachments, adjustable flexion-extension and adduction-abduction capable attachment components, total surface-bearing or increased surface-bearing members, additional strut or additional control cross-link members, and/or any other appropriate additions. Members such as these are elaborated on in greater detail below.

Ischial Weight Bearing Seat Extension Members

Embodiments of ischial weight bearing seat extension members are extensions to the struts and/or the proximal brim described above. Such members are designed and shaped to allow for weight bearing or additional support or control of the prosthesis by fitting under or applying pressure to the inferior aspect and/or medial aspect of the ischial tuberosity. This anatomical structure is a well-established weight bearing area, and is a pressure tolerant area for many amputees. Additionally, because of its connection with the spinal column, it serves as an effective means for stabilizing the prosthesis and controlling the prosthesis as the amputee moves his or her body. Since the anatomical shape and size of amputees varies, as well as their pressure sensitivity and needs, the ischial weight bearing seat extension members may vary in pre-fabricated sizes and shapes. Additionally, such a member may be custom fabricated or be prefabricated, with part or the entire member formed from a moldable and/or adjustable material. The member may be used with the prosthetic system described above for different amputation levels, but will be most applicable for transfemoral amputees and hip-disarticulation amputees. The member may be attached and adjusted in any appropriate manner. Adjustment or function of the additional member may be automated or manual.

Tendon Bearing Extension Members

Embodiments of tendon bearing extension members may include extensions to the struts and/or the proximal brim described above. Such members are designed and shaped to allow for weight bearing or additional support or control of the prosthesis by applying pressure to one or more tendons. For example, for trans-tibial amputees, the patellar tendon is well established as a weight bearing or weight tolerant area. Therefore, the bearing extension members can be specifically configured and fit to apply pressure at the patellar tendon in order to distribute pressure from weight bearing at a pressure tolerant area. Since the anatomical shape and size of amputees varies, as well as their pressure sensitivity and needs, the bearing extension members may vary in pre-fabricated sizes and shapes. Additionally, this member may also be custom fabricated or be prefabricated, with part or all of the member formed from a moldable and/or adjustable material. The member may be used with the prosthetic system described above for different amputation levels, but will be most applicable for trans-tibial amputees. The member may be attached and adjusted in any appropriate manner. Adjustment or function of the additional member may be automated or manual.

Supercondular Extension Members

Embodiments of supercondular extension members can be extensions to the distal cup, struts, and/or the proximal brims described above. Such members are designed and shaped to allow for suspension and/or additional support or control of the prosthesis by applying pressure to one or more of the areas directly proximal to or above the condyles of the amputated bone, adjacent bone, or proximal bones. For example, trans-tibial amputees with short residual limbs or limbs with redundant tissue sometimes need additional medial-lateral control in order to adequately control the prosthesis. Therefore, the supercondular extension members can be specifically configured and fit to apply pressure at the area directly proximal to or above the condyles of the femur in order to distribute pressure from weight bearing at a pressure tolerant area. Since the anatomical shape and size of amputees varies, as well as their pressure sensitivity and needs, the supercondular extension members may vary in pre-fabricated sizes and shapes. This member may also be custom fabricated or prefabricated, with part or the entire member formed from a moldable and/or adjustable material. The member may be used with the prosthetic system described herein for different amputation levels, but will be most applicable for trans-tibial amputees, Symes amputees, wrist-disarticulation amputees, and trans-radial amputees. In some cases, it may be necessary to have an additional members associated with the supercondular extension members to allow for the supercondular section to be adjustable and/or removable. Adjustability can provide the advantage of being able to vary how much support or control is used, and/or removability of the supercondular extension members can be required for donning and doffing. The member may be attached and adjusted in any appropriate manner. Adjustment or function of such an additional member may be automated or manual.

Support or Control Extension Members

Embodiments of support or control extension members may include any one or multiple extensions to any other members or part therein. The members are designed and shaped to provide or aid in suspension and/or additional support or control of the prosthesis. Such a member may be attached and adjusted in any appropriate manner. Adjustment or function of such an additional member may be automated or manual. Since the anatomical shape and size of amputees varies, as well as their pressure sensitivity and needs, support and control members may vary in pre-fabricated sizes and shapes. Additionally, this member may also be custom fabricated or be prefabricated, with part the member or the entirety of the member being formed of a moldable and/or adjustable material. The member may be used with the prosthetic system described herein.

Sensor Members

Embodiments of sensor members may include an additional member of the modular and adjustable prosthetic system that allows for some form of determination or calculation of the amount of force, torque, load, and/or pressure being applied at one or more members and/or parts and/or portions of members. The force sensor member can sense, determine, or calculate the amount of force, torque, load, and/or pressure in many different ways, including, by way of example, in-line load cells, pancake load cells, rotary shaft torque sensors, and flush threaded pressure sensors. Data that is collected from the sensors may be relayed to a remote or onboard microprocessor unit for immediate or future use, and/or stored or saved remotely or onboard the modular and adjustable system. The member may be attached and adjusted in any appropriate manner. Adjustment or function of such an additional member may be automated or manual.

Inclinometer Members

Embodiments of inclinometer members may be integrated with or added to the modular and adjustable prosthetic system. Such a member may be attached and adjusted in any appropriate manner. Adjustment or function of the additional member may be automated or manual. Measurements of angles with respect to gravity for the prosthetic system can be used to help avoid a fall for the amputee, or help with the ability to navigate stairs, ramps, hills, or other obstacles. These measurements may be relayed to a microprocessor unit that may be integrated into the prosthetic system, attached, and/or remote.

An inclinometer or clinometer is an instrument for measuring angles of slope (or tilt), elevation or depression of an object with respect to gravity. It is also known as a tilt meter, tilt indicator, slope alert, slope gauge, gradient meter, gradiometer, level gauge, level meter, declinometer, and pitch and roll indicator. Clinometers measure both inclines (positive slopes, as seen by an observer looking upwards) and declines (negative slopes, as seen by an observer looking downward).

Accelerometer Members

Embodiments of accelerometer members may be integrated with or added to the modular and adjustable prosthetic system. Such a member may be attached and adjusted in any appropriate manner. Adjustment or function of the additional member may be automated or manual. Measurements of acceleration for the prosthetic system can be used to help avoid a fall or accident for the amputee, or help with the ability to navigate stairs, ramps, hills, or other obstacles. These measurements may be relayed to a microprocessor unit that may be integrated into the prosthetic system, attached, and/or remote.

An accelerometer is a device that measures the proper acceleration of the device. This is not necessarily the same as the coordinate acceleration (change of velocity of the device in space), but is rather the type of acceleration associated with the phenomenon of weight experienced by a test mass that resides in the frame of reference of the accelerometer device.

Gyroscopic Members

Embodiments of gyroscope members may be integrated with or added to the modular and adjustable prosthetic system described herein. Such a member may be attached and adjusted in any appropriate manner. Adjustment or function of the additional member may be automated or manual. Measurements or maintaining orientation for the prosthetic system may be used to help avoid a fall or accident for the amputee, or help with the ability to navigate stairs, ramps, hills, or other obstacles. These measurements may be relayed to a microprocessor unit that may be integrated into the prosthetic system, attached, and/or remote.

A gyroscope is a device for measuring or maintaining orientation, based on the principles of conservation of angular momentum. In essence, a mechanical gyroscope is a spinning wheel or disk whose axle is free to take any orientation. This orientation changes much less in response to a given external torque than it would without the large angular momentum associated with the gyroscope's high rate of spin. Since external torque is minimized by mounting the device in gimbals, its orientation remains nearly fixed, regardless of any motion of the platform on which it is mounted.

Gyroscopes based on other operating principles may also be used, such as the electronic, microchip-packaged MEMS gyroscope devices found in consumer electronic devices, solid-state ring lasers, fiber optic gyroscopes, and extremely sensitive quantum gyroscopes.

Weight-Bearing Surfaces

A total surface bearing interface may augment the modular support frame of the modular member socket for those who require a circumferential or total surface-bearing prosthetic socket. The interface may also be utilized to increase the weight-bearing areas, but not necessarily provide total surface-bearing. This interface may vary in its material and application, but may include a light but strong nylon or composite material similar to those found in backpacks. It may be a curable material that may be set to a given shape, may be made from a low temperature material that may be molded directly over the residual limb, or may be made in any other suitable way. The material of the interface may be flexible or rigid, and may span part of the socket or the entire socket area. These interfaces may be fit within the modular socket, or they may be formed or ordered separately and then inserted. The means for integrating such an interface with the modular socket may vary, but may include an integrated or separately attached snap, Velcro, or ratchet system to lock it into place in the structural modular frame.

Flexible Inner Liners

Other versions of the invention may utilize flexible inner liners or flexible inner brims. These members may or may not be total surface-bearing, as described above, but may be made in a similar way as listed for the interface. A flexible brim may be fabricated separately after establishing the frame, or integrated, and provides added comfort at the brim of the prosthesis without needing to cover the entire residual limb. This allows for increased comfort without adding unnecessary weight to the prosthesis.

Combined Use of Pre-Fabricated and Custom-Fabricated Frame Members

The embodiments of the methods, resulting products, and designs described herein can be utilized as a hybrid of custom-fabricated and pre-fabricated members. Additionally, aspects of this modular method and system may be utilized to augment, add, or be compatible with traditional or common methods of fabricating a prosthesis. For example, a prosthetist may choose to fabricate using traditional means, but may want to incorporate an adjustable member from the modular method and system. Certain modular method members can be designed to work like this.

Typical embodiments described herein are custom made, custom assembled, and/or custom adjusted for optimal results, however, some embodiments include pre-made and preassembled version of the design could be ideal and self-contained without the need for alteration by a trained professional. This could be true for individual instances, or there could be an alternative embodiment of the general module that is user adjustable and otherwise prepared for application and use by the amputee. The alternative embodiments may utilize one or more aspects of the embodiments described herein.

Connecting and Adjusting Mechanisms

One or more of the parts, methods, members, or aspects within the overall invention described here may be utilized independently with other designs or methods. For example, one of the hinges, fastening mechanisms, ratcheting systems, adjustable systems, or automated control systems specially designed for this modular method of prosthetic sockets may be sold separately for integrated use with traditional fabricating methods.

Use of Low Durometer Silicone

Additional material, such as low durometer silicone, may be added to the inside of the modular members to provide a surface that will help to maintain suspension of the residual limb inside the socket and avoid pistoning of the residual limb.

Frame Member Features

The modular method may include one or more oval shaped structural struts that are different than previously discussed in that they are shaped such that their cross section looks like an oval or an almond with rounded ends. Advantages to this type of strut include that it could be strong yet light, that its rounded edges and dual convex outer surface shape provide an ideal pressure distribution and safe edge surface, the bulkiness is limited, and it has great ability for adjustability and compatibility. The almond shaped structural strut alternative may be solid or hollow, may vary in flexibility, material, adjustability (adjustability may come from material capabilities and/or mechanical design capabilities), size, and exact shape.

A standard or set of standards can be chosen and maintained as consistent in order to be compatible with accompanying members. For example, the almond shaped structural members may have a 1" width version and a 1.5" width version and be fabricated to work with compatible angular change members, hinges, adjustable hinges, joining members, crossbeam members, adjustable extensions, proximal brim connection members, distal member connection members, sensors, etc. For example, one almond shape structural strut member may be anchored to a distal base member with an adjustable hinge, then it may apply a medially directed force onto the patient's residual limb through the middle part of the residual limb. It may be joined with a [Upsilon]' type joining member that connects it with two other almond shape structural strut members who divert pressure away from the amputee's fibula head, and then join with the proximal brim member. The almond shape structural strut members may include pressure distribution pads that are adjustable with use of wedges, set screws, or other adjustable means.

The adjustability and compatibility of the almond shape structural strut members may include any one or more of the following: mechanical angular change capabilities (such as accordion type angular changes, tilt angular changes, bowing angular changes, twisting angular changes, etc.), conformability of material capabilities, and use of compatible connection members. For this embodiment or for any of the other embodiments described herein, one or more of the members involved in the modular method socket may also be utilized as a functional or aesthetic extension from the socket. For example, the type of oval or almond shaped strut system in this embodiment may also be utilized to extend past the distal socket member and thereby serve as a modular pylon system as well. Such a system may also become the foot or part of the distal components and terminal device. The advantage of such a system is that the whole prosthetic system then works as a comprehensive system, thereby improving energy transfer and efficiency. This embodiment exemplifies that these modular methods and members may be extended to the use of the entire prosthetic limb. Having a congruent system that works directly with the modular members of the modular method system provides an advantage over the current alignment components, joints, and terminal devices that are available. What is more, the almond shape structural strut members may be used for other significant applications such as, by way of example, orthotics, robotics, and human exoskeleton systems.

Dynamic Tightening or Compression

The modular method may include a dynamic tightening or compression from the struts. For example, spring loaded hinge members or other means of dynamic compression may be used to connect to strut members to provide a desired amount of compression on the amputee's residual limb. This can be desirable in that it can improve suspension and control of the prosthesis. This embodiment can also function similarly to a Chinese finger trap, in that the further the amputee's residual limb is pushed down into the modular socket, the more resulting suspension and snug fit the amputee receives.

Specialized Hinges and Adjustable Members

The modular method may include one or more specialized hinges or adjustable members that are specifically designed and selected to work with elevated vacuum socket systems utilized in prosthetics. For example, the modular hinges may be selected as being low-profile and free-motion so that the compression and fit that is established from the elevated vacuum system can be what determines the relative position and contours of the socket. In this example, the modular socket may be wider or narrower as needed, depending on the current size of the amputee's residual limb, while the elevated vacuum provides the appropriate amount of compression, control, and suspension. This is an advantage over the prior art in that the socket will more easily change with the amputee if the size or shape of their residual limb changes.

Microprocessor Members for Adjustability, Adaptability, and Operability

Embodiments of microprocessor members may include an additional member of the modular and adjustable prosthetic system that allows for some form of determination or calculation of the amount of force or pressure being applied at one or members and/or parts and/or portions of members. The force sensor member may sense, determine, or calculate the amount of force or pressure in a variety of ways. The member may be attached and adjusted in any appropriate or effective manner, either manually or automatically.

The microprocessor unit can be programmed to use these measurements to make appropriate changes in the socket for specific activities, aid in controlling components distal to the prosthetic socket (such as a knee, foot, or elbow), or relay and collaborate with other sensors and control mechanisms distal to the socket. These are advantageous capabilities for prosthetic limbs, because they allow for orientation, angle, and positional information and adjustability options within, and at the level of, the prosthetics socket. The capability or capabilities of using one or more of the member options described above may be combined with microprocessor and sensor capabilities at the distal componentry to provide a new level of artificial limb awareness and ability. The advantage of the system having orientation, angle, and positional information and adjustability options is beneficially analogous to normal human locomotion, which also uses neural sensors and the central nervous system to process this information in order to know how to move and react to the surroundings properly.

The modular method may include one or more microprocessor control options that are designed and programmed to communicate and work together or in conjunction with other components of the prosthesis. For example, microprocessors utilized to adjust the fit and function in the socket may communicate with the prosthetic knee and/or prosthetic foot. Fit can be customized are adaptable as may be appropriate for a specific activity, environment, or position of the prosthesis. For example, an amputee may need his or her socket to fit more snugly when they are running in order for the socket to be more safe and secure, or the socket may automatically loosen at the posterior when the amputee is sitting, for increased comfort.

Embodiments of automated or manual controlling members may include an additional member of the modular and adjustable prosthetic system that provides means for controlling, moving, limiting, or guiding one or more members and/or parts and/or portions of members. For example, the automated controlling members may be a motorized hinge system that automatically controls the angle of the strut member in relation to the distal cup by a motorized ladder and ratchet system controlled by the microprocessor. Alternatively, the manual controlling members may be a hand driven ratchet and ladder system or an adjustable hinge mechanism. The automated or manual controlling members may be integrated into one or more of the other members described herein. The member may be attached and adjusted in any appropriate manner.

Microprocessor control may be utilized to control the adjustability or movement of one or more of the members involved in the modular member socket. For example, one or more automated control hinges may be controlled by a microprocessor. This microprocessor may collect data from sensors inside the socket and/or outside the socket, and have an option of communicating with other microprocessors such as microprocessor-controlled knees and feet. These data may then be used to adjust the socket fit to be appropriate for the needs of the patient. For example, if the patient starts running, the socket may tighten to increase control and suspension, or if the patient is sitting, the socket can loosen for increased sitting comfort.

Microprocessor control and other aspects of the modular system may be incorporated into other parts of the prosthesis and other systems beyond the socket per se. For example, the microprocessor that helps to control movements or adjustments in the socket may communicate with and cooperate with other parts of the prosthesis, such as the knee and foot. The modular socket design may incorporate an adjustable tension cable that is integrated with and adjusted at the level of the modular alignment pylon. Additionally, the connection member may be assembled with modular alignment members that are made specifically to add to or assist in the functioning of the modular socket system.

Use of a Dynamic Jig in Fabrication of a Residual Limb Socket

The embodiments of the methods, resulting products, and designs described herein may also be utilized as dynamic jig methods for setting processes of a direct fit system and/or as a casting aid for a prosthetic socket. For example, the same or similar modular members described herein to make a finished socket may also be used as a way to form a weight-bearing cast or mold of the residual limb or a direct fit socket. This may be especially useful when a total surface-bearing socket is required or preferred. The direct fit socket may be made of a carbon, fiberglass, Kevlar, or composite material with pre-impregnated resin that may be catalyzed at the desired time with UV, water, or other suitable means. Other novel and specialty aspects to this direct fit material and method may be incorporated, such as a trimmable and rollable edge, the ability to heat relieve and adjust the socket, the ability to have built-in modular and adjustable options, and the ability to have selected rigidity in selected areas. This system is advantageous over prior art in that it allows for static and dynamic testing for the comfort of the socket before the socket is hardened. Therefore, a patient can try the socket fit with the direct fit material in place and the modular members supporting and controlling the fit of the direct fit material in the appropriate locations, and then the socket may be adjusted using the modular method adjustability if the patient is experiencing discomfort anywhere. Then at the desired time, the direct fit socket may be catalyzed. The advantage that this method has over just sticking with the modular supporting frame is that it may allow for the socket to be lighter and less bulky without the supporting and adjustable features. Alternatively, a middle ground can be utilized where part of the modular frame is used, or part of the adjustability of the modular system is used and part of the direct fit sleek and light frame is used.

Residual Limb Measurement Approaches

The modular method may include a step of scanning, photographing, casting, three-dimensional point reference system, or other means of obtaining a three-dimensional digital or physical representation of the residual limb. A physical or digital positive representation of the amputee's residual limb may then be utilized to fabricate one or more custom contoured members, such members including, for example, custom fabricated struts, connecting members, adjustable members, distal base members, proximal brim members, or any other member. These custom members may be manufactured using direct manufacturing, three-dimensional printers, lamination, injection molding, or other suitable or preferred manufacturing or fabricating methods. In any case, the end product is a custom modular prosthetic socket that is then fit directly to the patient.

This alternative embodiment of the present invention offers the option of custom making the members based on that positive representation and other patient evaluation information, such as weight and activity level, with the expense of adding complexity, time, and cost to the process of creating the modular method socket. This alternative embodiment may be ideal for certain cases where custom fit and custom adjusted premade members will not serve the needs of the patient. It may also be chosen when the increased complexity, time, and cost are not an issue.

This alternative embodiment of a custom modular prosthetic socket still has advantages over the prior art in that it reduces the complexity of fabrication, because the same manufacturing techniques, machines, and materials used for the premade members may be used to fabricate the custom made members. They may be fabricated as individual members, then assembled and adjusted to meet the patient's needs. The alternative embodiment still offers the advantages that come with modular methods, as well as increased adjustability by both the practitioner and the patient. The modular methods make it easier to get a good fit of the prosthetic socket because of the inherent adjustability and modularity of the socket after fabrication takes place.

Covers and Fairings

Embodiments of a modular method socket, as provided herein, may include a cosmetic cover or aesthetic fairing. This cosmetic cover or aesthetic fairing may be made to connect to and be compatible with the rest of the modular method socket. This cosmetic cover or aesthetic fairing may be complex and expensive when made with state of the art materials, or relatively simple and inexpensive when made with low-cost materials. For example, prefabricated wrap-around cosmetic covers that are in the shape of a calf may be made of color appropriate low-density polyethylene to produce a low cost, water resistant, and durable solution.

Incorporation of Advanced Materials and Available Materials

The embodiments of the methods, resulting products, and designs described herein may be manufactured with advanced materials and manufacturing techniques and/or precision machinery, including 3D printing technology.

Other versions may utilize desired combinations of newly invented and previously introduced materials, manufacturing capabilities, joints, hinges, user adjustability, microprocessor control, automated or manual adjustment control, adjustable options, and other emerging technologies. Being able to utilize these emerging technologies and specialized parts that can be manufactured in a selected and interchangeable way, then incorporated into the basic modular prosthetic socket method, is one of the benefits of this method and an advantage over the prior art. This modular system can more easily incorporate new technology.

The embodiments of the methods, resulting products, and designs described herein may be manufactured with basic materials and manufacturing techniques that can be made in affordable and locally sustainable ways. This can be ideal for developing world applications. Alternative forms of the invention include using low-cost, sustainable, and locally available materials (such as bamboo) for developing country applications. This can be especially beneficial for the tens of thousands of amputees who go without prostheses in developing countries. Other aspects to the present invention, like easier training, faster deployment, less space, fewer tools, and the like, make the present invention applicable to developing countries and relief situations. The desired method of distribution can be something like what is done with the Tom's Shoes system, where for each modular method prosthesis or prosthetic socket that is purchased in a developed country; someone who cannot afford a limb gets fit with one in a developing country.

Particular Advantages of Embodiments of the Invention

The following aspects of the invention, as provided herein, may be understood as being advantageous, with particular reference to conventional fabrication processes that are reliant on molding steps or on direct fit limb socket approaches that have been attempted to this point.

1. Method embodiments of the invention, as described herein, are highly efficient in terms of required time and resources. These aspects of the invention favor it economically, within any economy, but the relevance is increased in environments where resources are limited.

2. Embodiments of the invention little space and little machinery to deliver custom-fitted sockets. These advantages have particular relevance in emergency relief situations where infrastructure has yet to be reestablished following a natural or man-made disaster.

3. Embodiments of the invention provide adjustability features that extend beyond the capabilities associated with a bivalve arrangement, telescoping features, or circumferential wrapping design. In particular, the adjustability of the socket may be assembled for a changing pressure profile that matches the patient's changing needs over time.

4. Embodiments of the invention provide the capability for the residual limb socket to adjust for volume fluctuation in the residual limb, and are highly adaptable for different limb sizes and shapes. This is due to the fact that the individual members are selected and assembled to meet the needs of the individual amputee. Hence, the angles and contours of the selected members may be oriented and assembled to meet the needs of virtually any amputee.

5. Embodiments of the invention require relatively brief training for successful delivery and follow-up. The method also has a relatively low level of complexity for what the trained healthcare professionals are required to do in order to fabricate and fit the amputee.

6. Embodiments of the invention advantageously provide for enhanced ability to dissipate heat and perspired and environmental moisture.

7. Embodiments of the invention are highly adaptable or compatible to any given or conventional mechanism by which suspension of the prosthetic is achieved.

8. Embodiments of the invention, as methods for making a residual limb socket do not necessarily require electrical power to implement.

9. Embodiments of the invention are advantageously able to use desired combinations of conventional and new materials, joints, hinges, user adjustability, the microprocessor control, automated or manual adjustment control, and adjustable options. The specialized parts may be manufactured in a selected and interchangeable way that is easier to manufacture than current designs.

10. Embodiments of the invention allow for user empowerment and control regarding adjustability, repair, and other user controllability over the operability of their prosthetic socket and complete assembly, as may be appropriate.

11. Embodiments of the invention provide a quick route to get the product to a point of a trial fitting on the amputee, and to make changes as may by appropriate per the trial fitting.

12. Embodiments of the invention have a modular assembly aspect that allow it to adapt and work well with emerging surgical, biological, and technical advancements, as represented, for example, by implants and osseointegrated devices.

13. Embodiments of the invention, by virtue of having a short manufacturing time, release available time for training, therapy, and instructions on care, use, and follow-up. Allowing more time to address these goals positively affects patient outcomes.

14. Embodiments of the invention allow for various types of socket shapes and various options for pressure profile distribution, as well as the modular and adjustable ability to change as the patient changes.

15. Embodiments of the invention may utilize CAD/CAM technology, scanning and imagery technologies, and other shape capturing technology, as well as 3D printing and other manufacturing technology.

16. Embodiments of the invention, in the absence of mold-related steps and in view of minimal fabrication time, offer the ability to test the prosthesis under its intended weight-bearing conditions.

Illustrated Embodiments

FIG. 1 is a perspective view of an example of a right above-knee (trans-femoral) prosthetic socket after the modular members have been selected, assembled, formed, and adjusted to fit over an individual's residual limb. Item 1 of FIG. 1 is an example of a proximal brim member specially fabricated and engineered for the anterior-medial aspect of the proximal brim for an above-knee (trans-femoral) modular prosthetic socket after it has been formed directly to match the individual's residual limb. Item 2 is an example of a proximal brim member specially fabricated and engineered for the ischial aspect of the proximal brim after it has been formed directly to match the individual's residual limb wherein it is engineered and fabricated to be able to form for socket ischial containment. Item 3 is an example an encircling band after it has been formed directly to match the individual's residual limb. This particular example is a semi-rigid and formable male telescoping member of an encircling band after it has been formed to the individual's residual limb. This particular example of an encircling band is an encircling band that is engineered to be able to manually tighten or loosen as enabled by the rotary tensioning mechanism 12 and internal tensioning cables that run through the inside of the encircling band 3. Item 4 is an example of a semi-rigid and formable female telescoping section of the encircling band after it has been formed directly to the individual's residual limb. Item 5 is an example of the inner surface of a strut after it has been formed directly to the individual's residual limb. This inner surface has an appropriate material to match the individual's needs such as a silicone pad for suspension and shock absorption as well as lateral moisture wicking materials. Item 6 is an example of a second encircling band after it has been formed directly to match the individual's residual limb. A second encircling band has been added in this example as a way to increase socket strength and strength of adjustability for a high activity individual. Item 7 is an example of a strut after it has been formed directly to contour to the individual's residual limb. Item 8 is an example of a distal cup member after it has been formed directly to fit the individual's residual limb. Item 9 is an example of a set screw for strut telescoping mechanism 10 used to set the desired height of the strut wherein the height of the strut can be adjusted to match the needs of the individual person's residual limb. Item 13 is two examples of a proximal brim member specially fabricated and engineered for the lateral aspect of the proximal brim for an above-knee (trans-femoral) modular prosthetic socket after they have been formed directly to match the individual's residual limb. Item 21 is an example of a distal attachment member, to which distal ends of the struts 7 are attached, and which is described in more detail in reference to FIGS. 2 and 3.

FIG. 2 is a perspective view of an example of a right above-knee (trans-femoral) prosthetic socket after the modular members have been selected, assembled, molded, but before it has been directly molded and adjusted to fit over an individual's residual limb. Item 14 of FIG. 2 shows two examples of a proximal brim member specially fabricated and engineered for the lateral aspect of the proximal brim for an above-knee (trans-femoral) modular prosthetic socket before they have been formed directly to match the individual's residual limb. Item 15 is an example of a proximal brim member specially fabricated and engineered for the ischial aspect of the proximal brim for an above-knee (trans-femoral) modular prosthetic socket before it has been formed directly to match the individual's residual limb. Item 22 is an example an encircling band before it has been formed directly to match the individual's residual limb. This particular section is an example a semi-rigid and formable female telescoping member of an encircling band before it has been formed to the individual's residual limb. This example of an encircling band is an encircling band that is engineered to be able to manually tighten or loosen as enabled by the rotary tensioning mechanism, 12 and internal tensioning cables that run through the formable male, 23 and female, 22 telescoping members and connect to the tensioning mechanism. Item 18 is an example of a strut in its prefabricated form before it has been formed directly to match the individual's residual limb. Item 19 is an example of a distal cup in its prefabricated form before it has been formed directly to match the individual's residual limb. Item 20 is an example of distal portion of a strut wherein this particular strut type has a metal base which connects at an assembled distal attachment member 21 This particular type of distal portion of a strut 20 is designed to be adjustable in the angle by which it is mounted to the distal attachment member 21 as well as being directly formable to the individual. The compatible and adjustable relationship between this distal portion of the strut 20 and the assembled distal attachment member 21, is also an example of how the overall modular prosthetic socket is engineered such that the separate specialized members that can be selected from an inventory of specialized members to custom match the end user's needs are engineered to be compatible and/or adjustable to one another wherever appropriate. Item 24 is an example of an inside surface of a strut before it has been formed directly to match the contours of an individual's residual limb and/or cut to an appropriate length for the individual's residual limb. This inside surface of a strut member 24 includes a shock absorbing material such as silicone as well as including lateral wicking moisture channels. Like other strut surfaces, these surface materials are engineered for ease of replacement in order to provide simple methods to be able to add materials or components that offer specific properties or attributes that are beneficial for the end user. Item 25 is an example of a proximal brim member specially fabricated and engineered for the anterior-lateral aspect of the proximal brim for an above-knee (trans-femoral) modular prosthetic socket before it has been formed directly to match the individual's residual limb.

FIG. 3 is a frontal cross sectional view of an exploded right above-knee (trans-femoral) prosthetic socket. This embodiment provides encircling tensioning member with microprocessor control, outside t-nuts to enable encircling wrap of fiberglass casting tape or similar means to increase pressure distribution area in a directly formable and low-cost way as well as provide a location to attach a cosmetic cover. Item 15 of FIG. 3 is an example of a proximal brim member specially fabricated and engineered for the ischial aspect of the proximal brim for an above-knee (trans-femoral) modular prosthetic socket before it has been assembled and before it has been formed directly to match the individual's residual limb. Item 27 is an example of an insertion member of proximal brim member 15 wherein the insertion member is fabricated and engineered to be compatible with the insertion member of a proximal brim receiver 28 of the strut 18. The specific mechanism of mounting a proximal brim member to the proximal aspect of a strut may vary but this example demonstrates that the proximal brim members are fabricated and engineered to be able to mount to the proximal aspect of a strut. Item 22 is an example an encircling band before it has been formed directly to match the individual's residual limb. This particular section is an example a semi-rigid and formable female telescoping member of an encircling band before it has been formed to the individual's residual limb. This example of an encircling band is an encircling band that is engineered to be able to manually tighten or loosen as enabled by the tensioning mechanism 12 and internal tensioning cables that run through the formable male 23 and female 22 telescoping members and connect to the tensioning mechanism. Item 29 is an example of a t-nut which is mounted to the outside of strut 18 as a means to allow ease in attachment of a cosmetic cover, tensioning system, encircling ring, and/or to allow for the struts to be structurally reinforced as well as increased in their surface area by an external surface-bearing interface wrapping circumferentially around the external surface of the struts with a direct formable fiberglass casting tape or other applicable means for providing an increased weight bearing surface area or total surface-bearing addition to the struts in a way where the circumferential wrap can be easily fixed to the struts by grinding the casting tape down to the top of the t-nut after the casting tape has hardened and then screwing rounded bolts into the t-nuts, or for affixing other beneficial members. Item 20 is an example of distal portion of a strut wherein this particular strut type has a metal base which connects at an assembled distal attachment member 21. This particular type of distal portion of a strut 20 is designed to be adjustable in the angle by which it is mounted to the distal attachment member 21 as well as being directly formable to the individual. Item 30 is an example of the distal component of the resulting assembled distal attachment member 21 wherein this distal component of the resulting assembled distal attachment member 21 is fabricated and engineered such that it has a serrated channel 31 to accommodate being joined together with the serrated channel 31 of a proximal component 37 of the resulting assembled distal attachment member 21 in order to receive and attach the distal aspect of a strut 20 in the desired location and angle, as well as drilled holes to accommodate standard endoskeletal alignment components and moisture evacuation channel/s and/or suspension channel 33. Item 32 is an example of a distal attachment bolt which is used to join a modular alignment mechanism together with proximal and distal components of the resulting assembled distal attachment member 21. Item 33 is an example of a moisture evacuation channel/s and/or suspension channel which is incorporated into the assembled distal attachment member 21, distal cup, end pad, flexible inner liner and/or other distal members in order to allow the modular prosthetic socket to be compatible with existing methods of suspension such as shuttle locks and moisture management as well as allow for proprietary members for means of suspension and moisture management that the inventors are currently working on such as specialized locking mechanisms with air seal, one-way valve/s, and specialized moisture channels. Item 34 is an example of an attachment bolt which is used to join a distal cup together with an assembled distal attachment member 21. Item 35 is an example of a modular alignment component that is compatible with commonly used endoskeletal prosthetic alignment systems. Item 37 is an example of the proximal component of the resulting assembled distal attachment member 21 wherein this proximal component of the resulting assembled distal attachment member 21 is fabricated and engineered in order to receive and attach the distal aspect of a strut 20 in the desired location and angle, as well as drilled and tapped holes to accommodate standard endoskeletal alignment components, distal cup, and moisture evacuation channel/s and/or suspension channel 33. Item 38 is an example of a prefabricated direct formable distal end pad with a moisture evacuation channel/s and/or suspension channel 33 before it has been formed to the distal end of the residual limb such that it contours the distal end of the limb to avoid skin irritation and provides shock absorption for the individual user's residual limb. Item 19 is an example of a distal cup before it has been formed directly to match the individual's residual limb. Item 10 is an example of the strut telescoping mechanism wherein the height of the strut can be adjusted to match the needs of the individual person.

Figure 4:
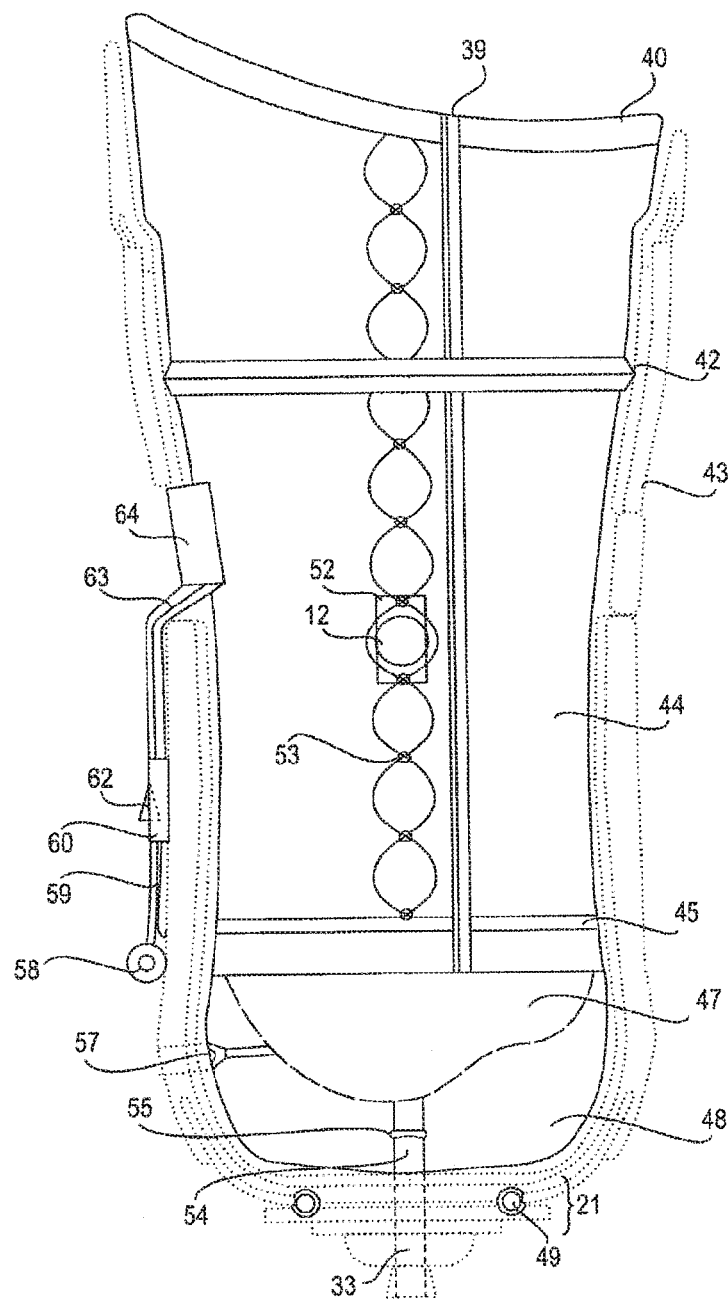
FIG. 4 is a frontal cross sectional view of the above-knee (trans-femoral) prosthetic socket shown exploded in FIG. 3 after it has been assembled and including a total surface-bearing flexible inner liner after it has been assembled and formed to the individual's residual limb.

FIG. 4 is a frontal cross sectional view of the above-knee (trans-femoral) prosthetic socket shown exploded in FIG. 3 after it has been assembled and including a total surface-bearing flexible inner liner after it has been assembled and formed to the individual's residual limb. Item 39 in FIG. 4 is an example of an adjustable seam for the directly formable wraparound longitudinal member of a direct formable total surface-bearing flexible inner liner 44 which allows the wrap-around type longitudinal member of a direct formable total surface-bearing flexible inner liner 44 to be wrapped around the longitudinal aspect of the limb and seal at an overlap for the appropriate circumference of the individual's residual limb after the distal cup member for the direct formable total surface-bearing and flexible inner liner 47 has been formed. Item 44 is also meant to point out the entirety of an assembled direct formable total surface-bearing flexible inner liner after it has been direct formed to match the size and contour of an individual's residual limb. Fabricating and engineering this directly formable wrap-around type longitudinal member provides the advantage that it can accommodate a wide array of limb shapes and sizes due to the wrap-around fitting method that it facilitates. Item 40 is an example of a proximal trimline for the directly formable wrap-around type longitudinal member of a direct formable total surface-bearing flexible inner liner 44 after it has been trimmed to match the residual limb length and functional needs of the individual's residual limb and after a non-abrasive and rolled edge has been incorporated into this proximal trimline 40. Item 42 is an example of an inner and outer sealing member for the directly formable wrap-around type longitudinal member of a direct formable total surface-bearing flexible inner liner 44 after it has been direct formed to the individual's residual limb wherein the inner and outer sealing member 42 aids in suspension of the residual limb. Item 43 is an example of an assembled modular prosthetic socket after the modular socket members have been selected and it has been assembled and then direct formed to match the needs of the individual and the individual's residual limb wherein the individually selected modular socket members of the modular prosthetic socket have been shown in an exploded view and individually called out in FIG. 3. Item 45 is a distal sealing member for the directly formable wrap-around type longitudinal member for a direct formable total surface-bearing flexible inner liner 44 wherein the distal seal allows for the directly formable wrap-around type longitudinal member for a direct formable total surface-bearing flexible inner liner 44 to be attached to and create an air-tight seal with the direct formable distal cup member for the direct formable total surface-bearing and flexible inner liner 47 after they have been directly formed to fit the individual's residual limb. Item 48 is an direct formable distal end pad of the direct formable distal cup member 47 that is fabricated and engineered to include means for direct forming to an individual's residual limb by allowing pre-filled air, foam, and/or other applicable contents to evacuate the sealed chamber by way of an expulsion valve as the end pad is pressed onto the distal end of the residual limb for direct forming. If the distal end of the residual limb gets smaller, air, foam, or other applicable material is allowed to re-enter the sealed chamber of the direct formable distal end pad 48 passively through the expulsion valve or it is injected with applicable contents until it meets the distal end of the amputee's residual limb. Therefore, this example of a direct formable distal end pad is not only custom shaped to the distal end of the individual's residual limb, it is also a custom end pad that can change with the individual as their limb changes with time. Item 49 is an example of an enclosed and assembled serrated channel with a distal portion of a strut is placed in the enclosed and assembled serrated channel 49 at the desired takeoff angle. Item 21 is an example of an assembled distal attachment member wherein the distal attachment members shown here is fabricated and engineered to be able to assemble in such a way that it can receive and securely mount the distal aspect of a strut as well as a distal cup and modular alignment components. Item 52 is an example of a microprocessor unit, means of communication linking between other independent sensors and microprocessors, and internal sensors wherein it has been joined with a rotary tensioning mechanism 12. This microprocessor unit and accompanying sensors and means of communication 52 allows for collection of data, communication of data, and interpretation of data that provides the ability for automated control of socket tightening and loosening by means of the rotary tensioning mechanism 12 as well as coordination between other microprocessors and/or sensors located in other places on the modular prosthetic socket or within distal componentry such as a knee, foot, elbow, and/or hand. This communication with one or more other microprocessor or sensors located on the modular prosthetic socket provides the ability for coordinated tightening, loosening, or other pressure profile changing means within different parts of the modular prosthetic socket such as the direct foldable flexible inner liner 44 and the side-mounted ratcheting lanyard suspension mechanism 64. This ability for the modular prosthetic socket to automatically tighten, loosen, or otherwise change its pressure profile and to do so in a coordinated way with different aspects of the allows for the modular prosthetic socket and direct formable flexible inner liner 44 to automatically change its pressure profile to match the user's preferences for specific activities such as sitting or running. While this particular example uses a rotary tension unit 12 and tensioning cables 53, as the means of pressure profile change, other means of pressure profile change are utilized to change the pressure profile such as phase changing materials, rheo magnetic fluid materials, ratcheting device/s, pulley systems, by application of heating or electrical current to reform or change material properties, and/or other applicable means. Item 54 is an example of a moisture evacuation channel/s and/or suspension channel which is incorporated into the direct formable distal cup member 47 and direct formable distal end pad 48 to allow the modular prosthetic socket to be compatible with existing methods of suspension such as shuttle locks and moisture management as well as allow for proprietary modular socket members which offer means of suspension and/or moisture management. Item 55 is an example of an expulsion valve that can be used to expel air or fluid and is integrated into the moisture evacuation channel/s and/or suspension channel 54. Item 57 is an example of valve or port that enables use of an elevated vacuum system. Item 58 is an example of a pull cord for a side-mounted ratcheting lanyard suspension mechanism 64. Item 59 is an example of ratcheting teeth/tabs for a side-mounted ratcheting lanyard suspension mechanism 64. Item 60 is an example of a housing unit for a microprocessor controlled locking mechanism for a side-mounted ratcheting lanyard suspension mechanism 64, sensors, and means of communication with microprocessor 52 and/or other microprocessors. Item 62 is an example of manual release button for the locking mechanism for a side-mounted ratcheting lanyard suspension mechanism 64. Item 63 represents a socket exit port which allows the ratcheting lanyard to exit the modular prosthetic socket and feed into the microprocessor controlled locking mechanism 60. Item 64 represents the overall side-mounted ratcheting lanyard suspension mechanism and specifically points to where the side-mounted ratcheting lanyard suspension mechanism 64 is bonded to the direct formable total surface-bearing flexible inner liner 44.

Figure 5:
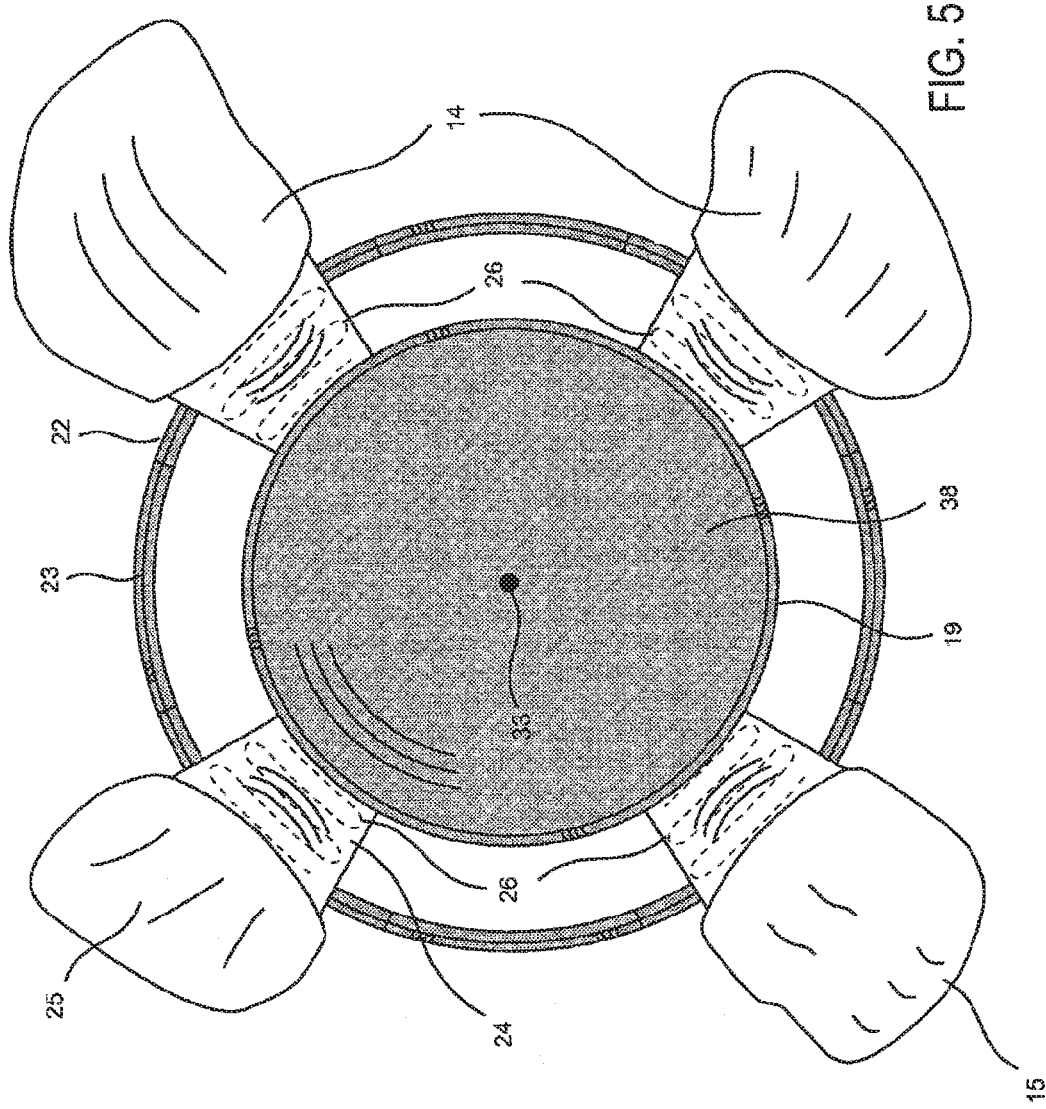
FIG. 5 is a top view of an example of a right above-knee (trans-femoral) prosthetic socket after the modular members have been selected, assembled, molded, but before it has been adjusted to fit over an individual's residual limb. This perspective gives a clear view of an encircling tensioning member without microprocessor control.

FIG. 5 is a top view of an example of a right above-knee (trans-femoral) prosthetic socket after the modular members have been selected, assembled, molded, but before it has been adjusted to fit over an individual's residual limb. This perspective gives a clear view of an encircling tensioning member without microprocessor control. Item 26 in this figure is an example of a heating coil which is embedded into the strut in order to allow for electrical current to pass through the heating coil 26 for the purpose of temporarily or permanently changing the properties of the strut. Item 14 shows two examples of a proximal brim member specially fabricated and engineered for the lateral aspect of the proximal brim for an above-knee (trans-femoral) modular prosthetic socket before they have been formed directly to match the individual's residual limb. Item 15 is an example of a proximal brim member specially fabricated and engineered for the ischial aspect of the proximal brim for an above-knee (trans-femoral) modular prosthetic socket before it has been formed directly to match the individual's residual limb wherein it is engineered and fabricated to be able to form directly for ischial containment. Item 19 is an example of a distal cup in its prefabricated form before it has been formed directly to match the individual's residual limb. Item 22 is an example an encircling band before it has been formed directly to match the individual's residual limb. This particular section is an example a semi-rigid and formable female telescoping member of an encircling band before it has been formed to the individual's residual limb. Item 23 is an example a semi-rigid and directly formable male telescoping member of the encircling band 22 before it has been formed directly to the individual's residual limb. Item 24 is an example of an inside surface of a strut before it has been formed directly to match the contours of an individual's residual limb and/or cut to an appropriate length for the individual's residual limb. This inside surface of a strut member, 24 includes a shock absorbing material such as silicone as well as including lateral wicking moisture channels. Like other modular surfaces material additions, these surface materials are engineered for ease of replacement in order to provide simple methods to be able to add materials or components that offer specific properties or attributes that are beneficial for the end user. Item 25 is an example of a proximal brim member specially fabricated and engineered for the anterior-lateral aspect of the proximal brim for an above-knee (trans-femoral) modular prosthetic socket before it has been formed directly to match the individual's residual limb. Item 38 is an example of a prefabricated direct formable distal end pad with a moisture evacuation channel/s and/or suspension channel 33 before it has been formed to the distal end of the residual limb such that it contours the distal end of the limb to avoid skin irritation and provides shock absorption for the individual user's residual limb.

Figure 6:
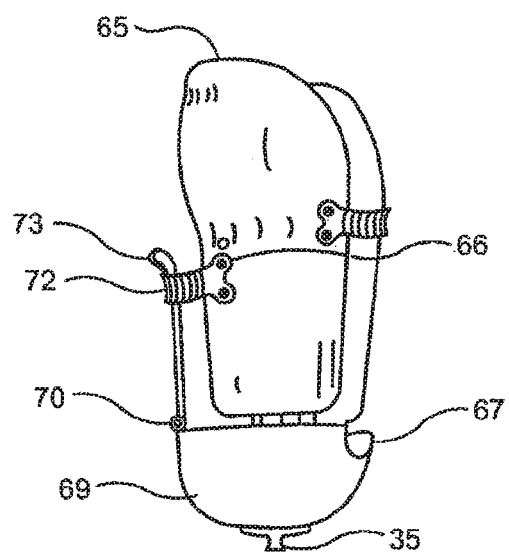
FIG. 6 is a perspective view of an example of a below-knee (trans-tibial) prosthetic socket.

FIG. 6 is a perspective view of an example of a below-knee (trans-tibial) prosthetic socket. Item 65 in this figure is an example of a proximal-medial brim member of the trans-tibial modular socket. Item 67 in this figure is an example of a relief cut-out for the distal tibia in the distal base member of the trans-tibial modular socket. Item 66 is a joining member between a medial strut member and proximal brim member 65 that allows height and angular adjustment by use of sliding and wedging. Item 70 is an adjustable strut to distal cup attachment mechanism. Item 35 is a standard alignable modular pyramid connector that is made to attach to the distal cup 69. Item 72 is a ratcheting adjustable member. Item 73 is the flared aspect of the posterior strut member of the socket that is specifically designed for allowing for knee range of motion.

Figure 7:
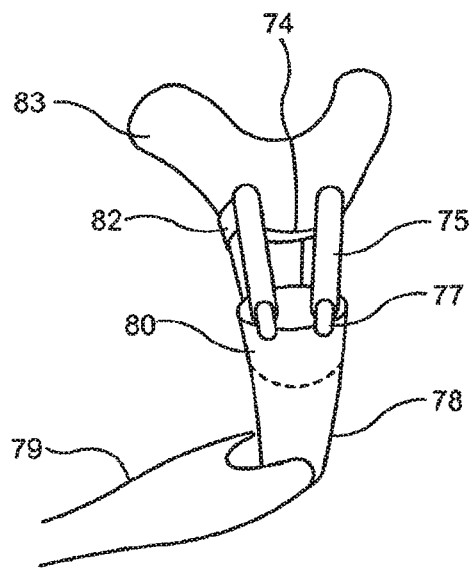
FIG. 7 is a perspective view of an example of an above-elbow (trans-humeral) prosthetic.

FIG. 7 is a perspective view of an example of an above-elbow (trans-humeral) prosthetic. Items 78 and 79 are the humeral and forearm sections, respectively, of the prosthesis that are connected to the modular socket. Item 74 is a sliding joint that may be used to adjust anterior-posterior fit of the socket. Note the difference between the strut 32 in FIG. 7 and adjustable telescoping strut 85 in FIG. 8, demonstrating the option of including strut member 85 that is adjustable in length via telescoping and strut 75 that may be cut to length but are then a fixed length. Item 77 is an adjustable attachment member used to attach strut 75 to distal cup 80. Item 82 is a cross-strut member that attaches to the anterior two struts of this modular prosthetic socket in a horizontal orientation with respect to the long axis of the amputated humerus bone for the purpose of optimizing biomechanical control in flexion of the amputated humerus bone.

Figure 8:
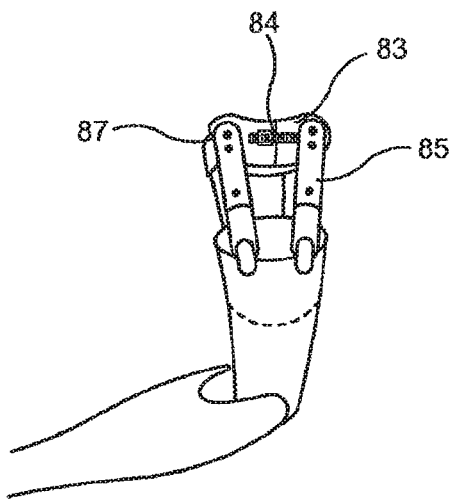
FIG. 8 is a perspective view of the same prosthetic sock as seen in FIG. 7, after the after the proximal brim member 83 of FIG. 7 has been molded and trimmed to produce the formed and trimmed proximal brim member 83 of FIG. 8 in order to allow for increased range of motion.

FIG. 8 is a perspective view of the same prosthetic sock as seen in FIG. 7, after the after the proximal brim member 83 of FIG. 7 has been molded and trimmed to produce the formed and trimmed proximal brim member 83 of FIG. 8 in order to allow for increased range of motion. Moreover, FIG. 8 shows an example of the same modular socket as in FIG. 7 wherein an addition of a horizontally oriented adjustment member 84 offers greater user-adjustability by means to tighten or loosen the proximal brim and proximal aspects of the included telescoping strut 85. Adjustable proximal brim to strut attachment mechanism 87 has also been added for increased adjustability as compared to the modular socket of FIG. 7. Hence, FIG. 8 in comparison with FIG. 7 offers an example of how modular socket members can be added, changed, and/or adjusted to accommodate the needs of the individual amputee.

Figure 9:
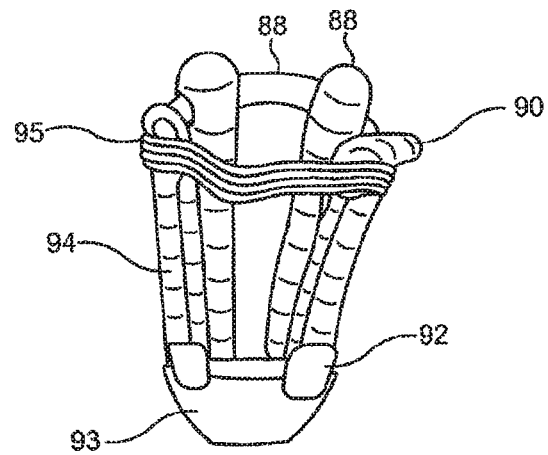
FIG. 9 is a perspective view of an example of an above-knee (trans-femoral) modular prosthetic socket after it has been formed to an individual's residual limb, this particular example having a cut-out in the strut member that allows for an encircling band to sit flush.

FIG. 9 is a perspective view of an example of an above-knee (trans-femoral) modular prosthetic socket after it has been formed to an individual's residual limb, this particular example having a cut-out in the strut member that allows for an encircling band to sit flush. Item 95 shows a cut-out in the strut member 94, which allows for the encircling band 88 to sit flush. The encircling band 88 serves as an adjustment member/tensioning member for the proximal brim of the modular prosthetic socket. Item 89 shows a proximal brim member for the lateral-posterior portion of the socket. Item 92 shows an adjustable attachment member which attaches a strut to the distal cup 93. Item 90 shows a proximal brim member that is specialized to form an ischial weight-bearing seat.

Figure 10:
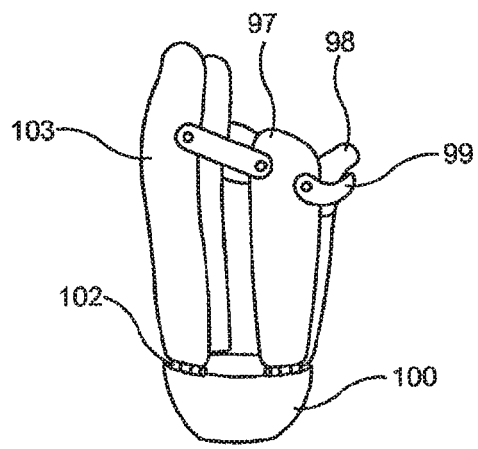
FIG. 10 is a perspective view of an example of an above-knee (trans-femoral) modular prosthetic socket after it has been formed to an individual's residual limb.

FIG. 10 is a perspective view of an example of an above-knee (trans-femoral) modular prosthetic socket after it has been formed to an individual's residual limb. Item 102 is an adjustable attachment member which attaches strut member 103 to the distal cup 100. Item 97 is a proximal brim member designed and molded directly to the user for the anterior-medial area of the proximal brim. Item 98 is a proximal brim member that is specially designed and molded directly to the user to accommodate ischial containment control of the user's residual limb. Item 99 is a non-adjustable proximal brim member that connects the ischial containment proximal brim member 98 to the anterior-medial proximal brim member 97.

Figure 11:
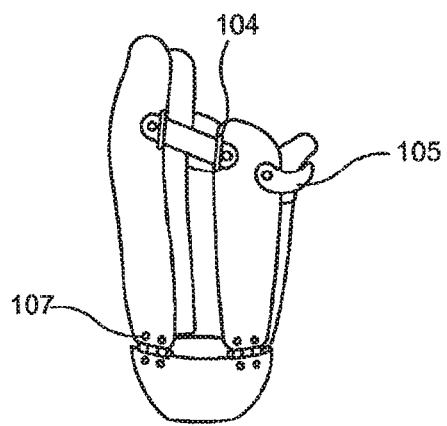
FIG. 11 is a perspective view of an example of a prosthetic socket of the present invention.

FIG. 11 is a perspective view of an example of a prosthetic socket of the present invention. This drawing is an example of the same right above-knee socket shown in FIG. 10, only the none-adjustable proximal brim member of figure has been replaced with adjustable proximal brim members 105 and 105. Item 107 shows an alternative means of affixing the adjustable attachment member which connects a strut to a distal cup wherein removable and recessed bolts are used.

Figure 12:
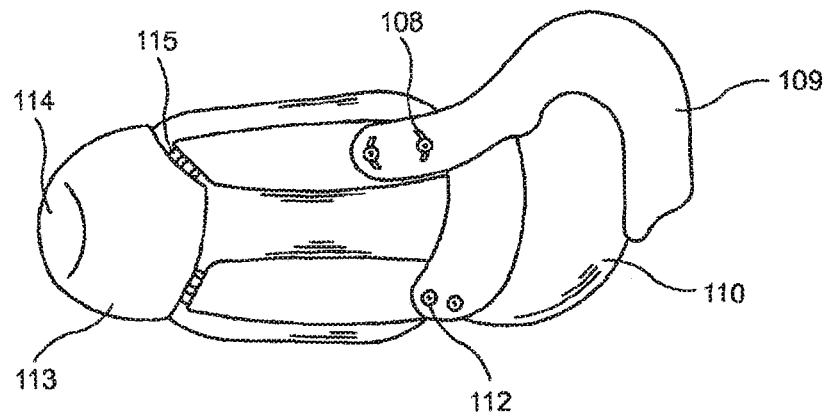
FIG. 12 is a perspective drawing of an example of a prosthetic socket of the present invention. This drawing is an example of a below-elbow socket, otherwise known as transradial prosthetic socket.

FIG. 12 is a perspective drawing of an example of a prosthetic socket of the present invention. This drawing is an example of a below-elbow socket, otherwise known as transradial prosthetic socket. Item 84 is an adjustment slot in proximal brim member 109 that allows for adjustability of the proximal brim member 109. Proximal brim member 109 also has means for adjustable supercondular clamping which is used as a means for support and suspension. Item 110 is a direct formable total-contact flexible inner liner which fits internally to the struts and proximal brim members and interfaces with the residual limb to increase pressure distribution. Item 115 is an adjustable attachment member. Item 112 is an attachment screw used as attachment means between a strut and a proximal brim member. Item 113 is a distal cup and item 114 is a distal attachment member.

Figure 13:
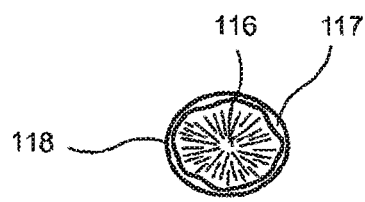
FIG. 13 is a superior view of the distal cup of the Symes (an ankle disarticulation socket) modular prosthetic socket as also seen in side view in FIG. 14.
Figure 14:
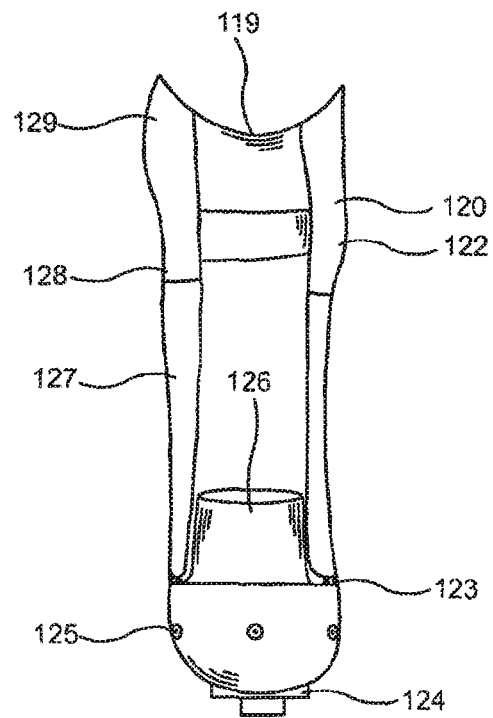
FIG. 14 is a side view of a prosthetic Symes socket (ankle disarticulation socket), showing, in particular, a height adjustable member with option for angular change.

FIG. 13 is a superior view of the distal cup of the Symes (an ankle disarticulation socket) modular prosthetic socket as also seen in side view in FIG. 14. Item 118 is a relief contour area of the distal cup and Item 117 is a compressive contour in the distal cup. These are examples that represent the fact that all members are specially contoured and designed for their specific applications. Item 116 is a moisture evacuation channel built into the distal cup.

FIG. 14 is a side view of a prosthetic Symes socket (ankle disarticulation socket), showing, in particular, a height adjustable member with option for angular change. This drawing is an example of a left Symes socket, otherwise known as an ankle disarticulation prosthetic socket after the modular members have been selected, assembled, molded, and adjusted to fit over an individual's residual limb. Item 128 is a height adjustable member with option for angular change. Item 126 is a distal push-in suction socket distal silicone cup. Items 125 are set screws that lock in the distal silicone cup 126. Item 122 is a relief for the fibular head on the residual limb of the amputee (not shown). Item 129 is a proximal brim member designed and molded to the residual limb of the amputee for the medial proximal aspect of the proximal brim. Item 119 is a proximal brim member designed and molded to the residual limb of the amputee for the patellar tendon area of the proximal brim. Item 120 is a proximal brim member designed and molded to the residual limb of the amputee for the lateral proximal aspect of the proximal brim. Item 123 is an adjustable attachment member. Item 124 is a distal attachment member. Item 129 is a proximal brim member used for the medial aspect of the socket. Item 127 is a strut formed and used for the medial longitudinal axis aspect of this prosthetic socket.

Figure 15:
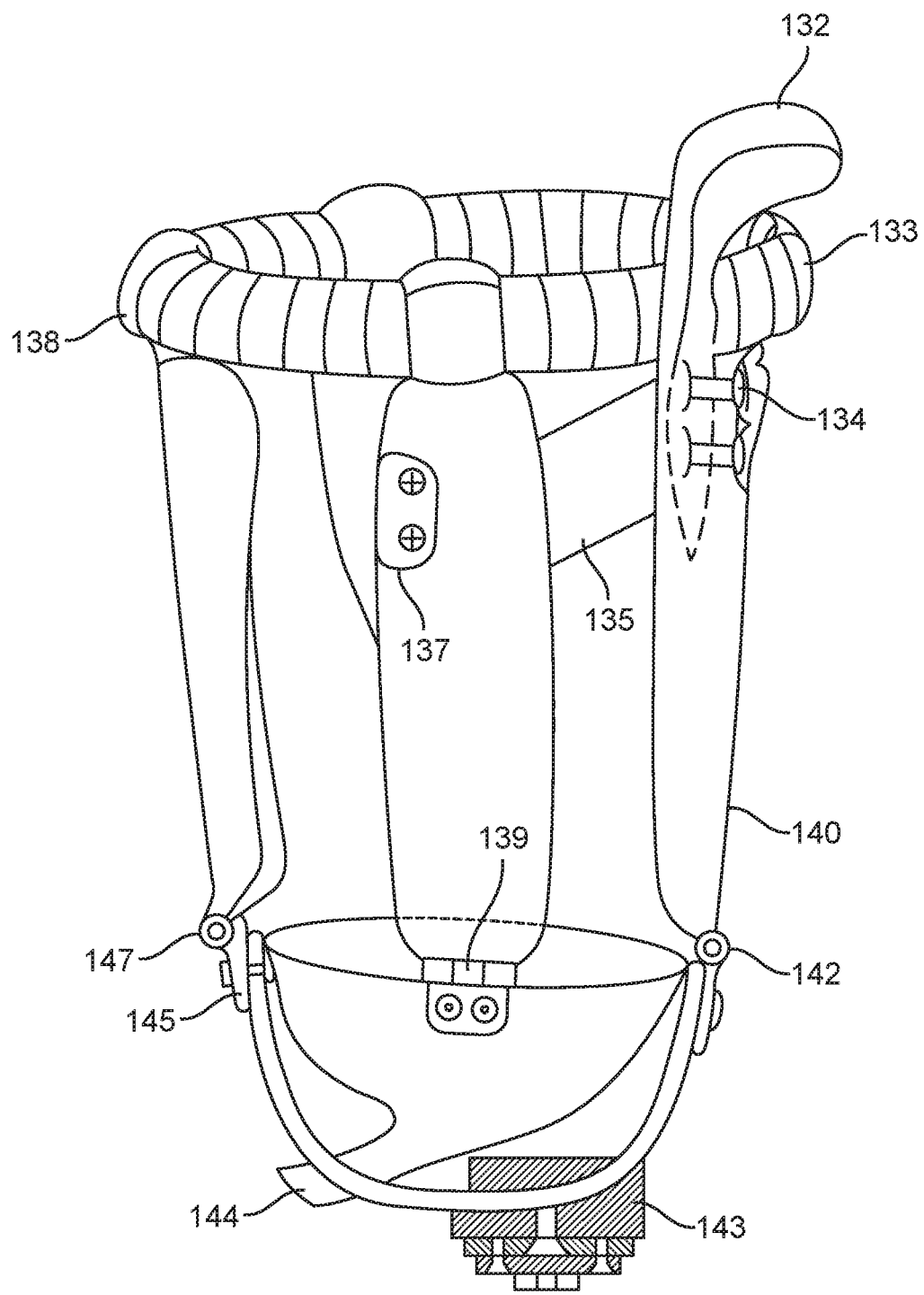
FIG. 15 is a perspective view of an above-knee (trans-femoral) socket that shows detail of a proximal brim with an adjustable section, as well as an ischial seat extension.

FIG. 15 is a perspective view of an above-knee (trans-femoral) socket that shows detail of a proximal brim with an adjustable section, as well as an ischial seat extension. This perspective drawing is demonstrating the opportunity for different members to be used and selected to match the needs of the individual. An adjustable encircling band 133 can be used to provide an adjustable proximal brim, or a fixed proximal brim 130 may be chosen. Item 132 is an ischial seat extension fastened with adjustable screws 134 and including a shock absorbing silicone pad. Item 135 is a cross-link member fixed to a strut by attachment means 134 and 137 connecting between two struts for added strength and biomechanical control. The adjustable encircling band 133 is a proximal brim member designed to allow for tensioning/adjustment of the proximal brim members. Item 128 is an attachment screw for added cross link member 135. Item 138 shows a joining mechanism of the proximal aspect of a strut which receives the adjustable encircling band 133 and allows it to be attached flush with the amputee's residual limb.

Figure 16:
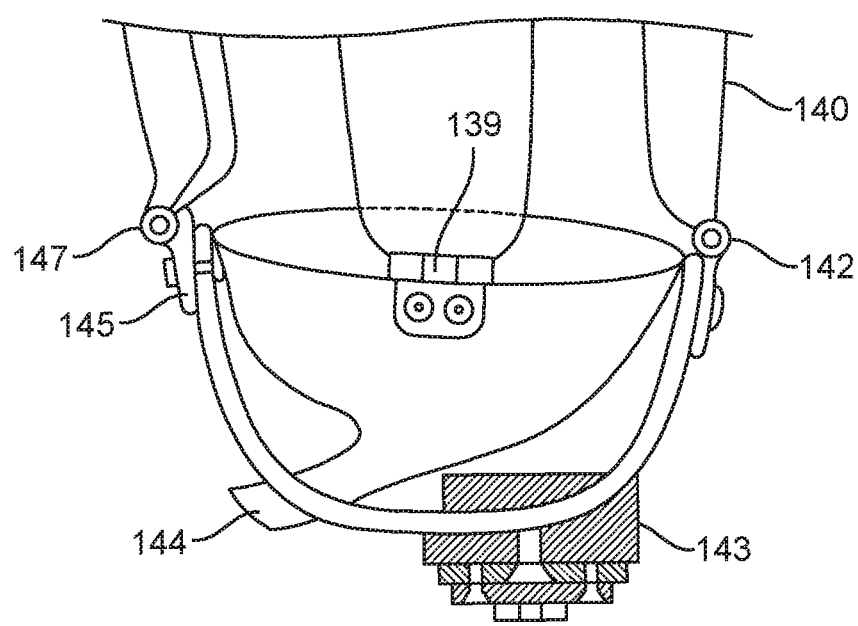
FIG. 16 is a perspective view of the distal portion of an above-knee (trans-femoral) prosthetic socket, showing detail related to an integrated suspension mechanism, and modular alignment feature and a settable hinge.

FIG. 16 is a perspective view of the distal portion of an above-knee (trans-femoral) prosthetic socket, showing detail related to an integrated suspension mechanism, and modular alignment feature and a settable hinge. FIG. 16 shows the ability for integrated suspension methods, such as item 144, an exit member for a suspension pull bag and location for mounting a suction valve. FIG. 16 further shows additional features that may be integrated into the modular prosthetic socket of the present invention to match the needs of the patient, such as adjustable alignment mechanism 143 and adjustable and settable (can be fixed at a desired position) hinges 139, 142, and 147. Item 140 is a strut. Item 145 is a bolt used as means for attachment of adjustable and settable hinge 147 to the distal cup.

Figure 17:
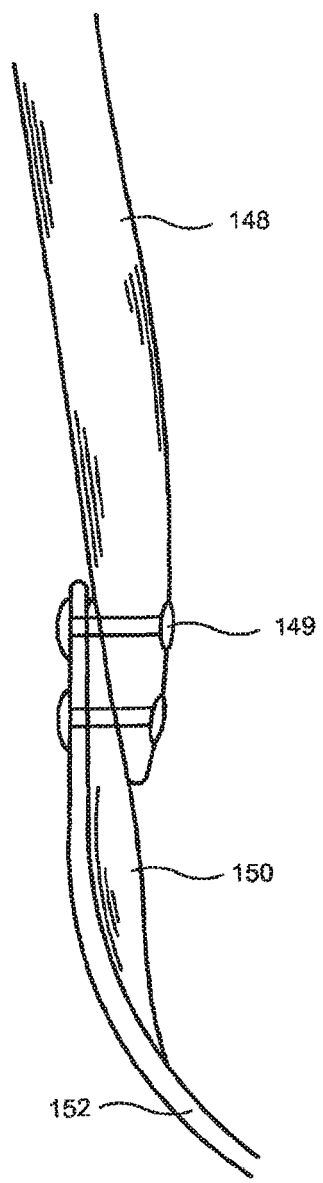
FIG. 17 shows lateral cross-section views of modular adjustable joint and hinge options, showing an option of utilizing wedges that may be removed or replaced to change the desired angle.
Figure 18:
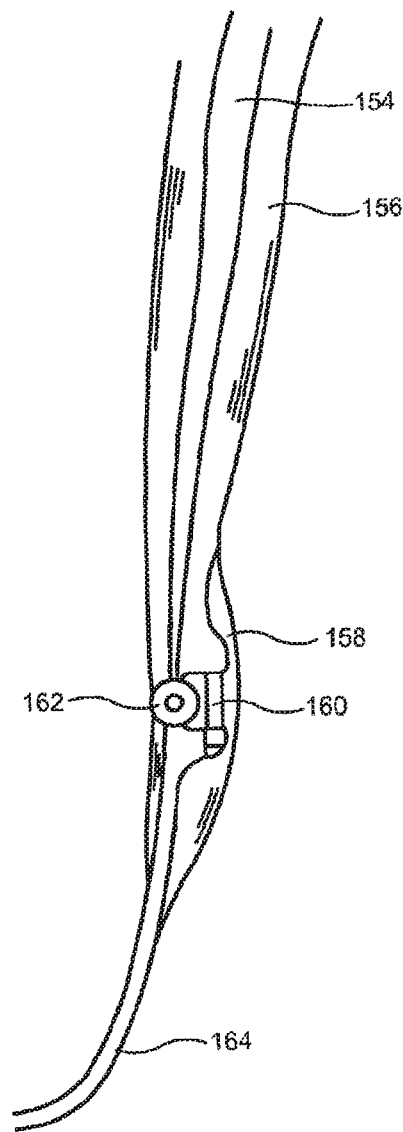
FIG. 18 shows a hinge with setscrew, hinge cover, and strut wedge.

FIGS. 17 and 18 are lateral cross-section drawings of specialized, proprietary, modular, and adjustable connection members that are fabricated and designed for specific purposes and can be utilized for the modular prosthetic sockets and methods described herein.

FIG. 17 shows lateral cross-section views of modular adjustable joint and hinge options, showing an option of utilizing wedges that may be removed or replaced to change the desired angle. Item 150 of this figure shows a wedge that can be removed or replaced to change the desired take-off angle of strut 148 relative to distal cup 149 and secured in place by attachment rivet 149.

FIG. 18 shows a hinge with setscrew, hinge cover, and strut wedge. FIG. 18 shows a hinge 162 with set screw 160 and hinge cover 158. Additionally, FIG. 18 shows the ability to add a wedge 154 or filler pad 154 to the strut itself 156.

Figure 19:
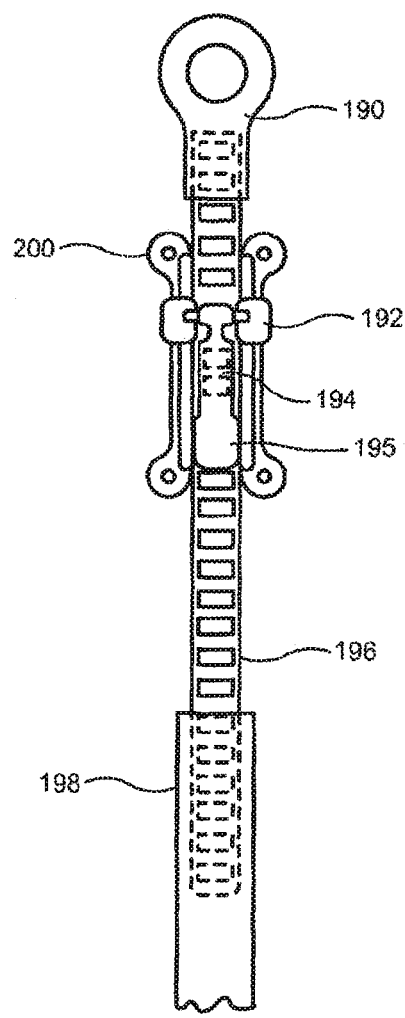
FIG. 19 is a superior perspective view of modular adjustable joint ratchet options that may be utilized for the prosthetic socket.

FIG. 19 is a superior perspective view of modular adjustable joint ratchet options that may be utilized for the prosthetic socket. Item 194 is a lock and release lever that snaps into a holding slot 195. The other numbered items are as follows: 190 is a means for the user to pull tension on the ratchet, 190 is the axis by which the lock and release lever 194 rotates, 196 is the portion of the ratchet strap which has holding slots 195 which can snap into the lock and release lever 194, 198 is the portion of the ratchet strap which connects to 196 and does not have holding slots 195 but can transfer or hold tension for the ratchet system. FIG. 16 shows a set screw 174 that can change the angle of the Y shaped strut 166 along with wedges such as wedge 168.

Figure 20:
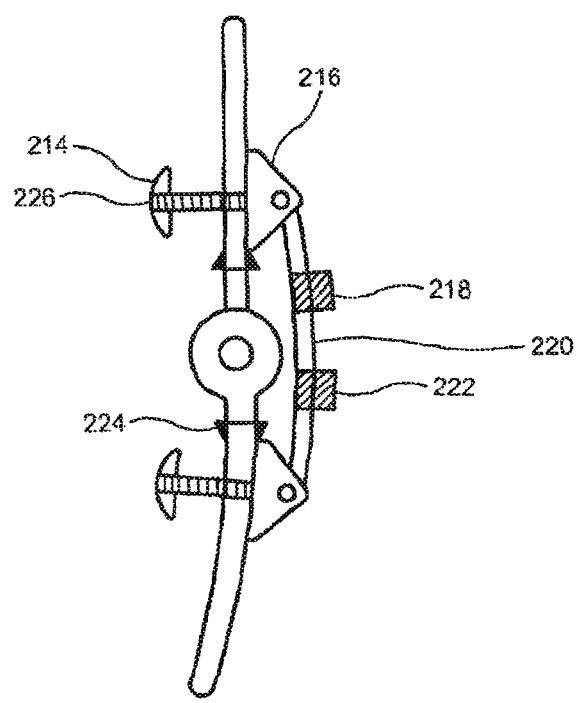
FIG. 20 shows an adjustable hinge with the additional features of retainer members as well as having the entire set beam member being a separate member that may be placed separately and set into place.
Figure 21:
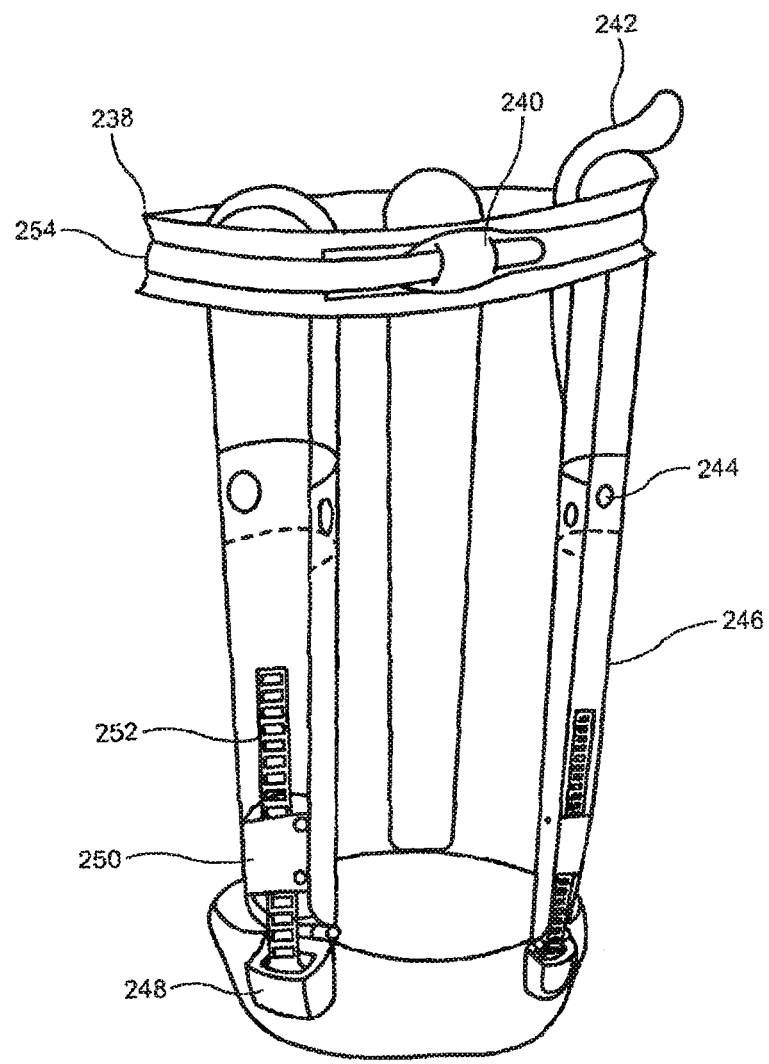
FIG. 21 is a perspective view of an example of prosthetic socket having an adjustable hinge member with microprocessor control.

FIG. 20 shows an adjustable hinge with the additional features of retainer members as well as having the entire set beam member being a separate member that may be placed separately and set into place. FIG. 21 shows an adjustable hinge similar to that of FIG. 20, with the additional features of retainer members 218 and 222 as well as having the entire set beam member 216 being a separate member that may be placed separately and set into place with elements 226 and 214. One advantage of this design is that this hinge may be integrated into a lamination wherein the center of the hinge may be blocked off using a dummy up against the sealing segments 224.

FIG. 21 is a perspective view of an example of prosthetic socket having an adjustable hinge member with microprocessor control. Item 250 shows where the microprocessor and control mechanism for the ladder 252 is located within the strut member 246 along with height adjustability of the strut 244. Proximal brim member 238 has been designed to allow for adjustability of strut members. Item 242 is a proximal brim member designed for ischial weight-bearing. Item 248 is an attachment and housing means for microprocessor control adjustable member. Item 254 is an adjustment strap member which along with adjustable member 240 provides means for adjustment of the proximal brim circumference so that the end user is empowered to tighten and loosen their own prosthetic socket manually.

Figure 22:
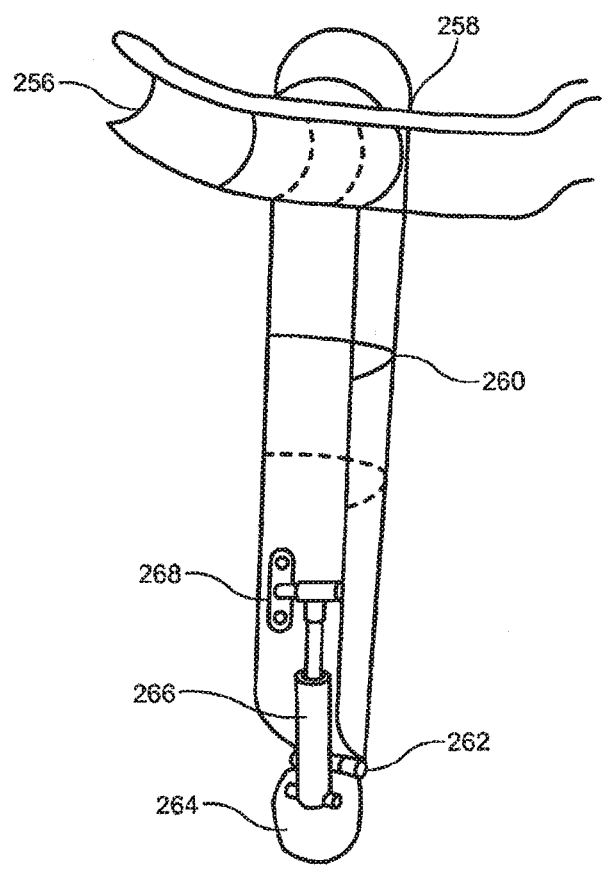
FIG. 22 is a perspective view of an example of a portion of a prosthetic socket having an adjustable member with microprocessor control.

FIG. 22 is a perspective view of an example of a portion of a prosthetic socket having an adjustable member with microprocessor control. This figure shows an alternative control method for a microprocessor hinge 262 as compared with the microprocessor controlled hinge of FIG. 21. This control method uses a hydraulic or pneumatic piston 266 that attaches to the strut at axis 268 in order to move the angle of the strut 260 to a desired position. Item 264 is a housing mechanism for the microprocessor and location of attachment to the distal member/s of a modular prosthetic socket. Item 260 is an adjustable height mechanism. Item 258 is a recessed portion of the strut to accommodate an encircling ring 256.

Figure 23:
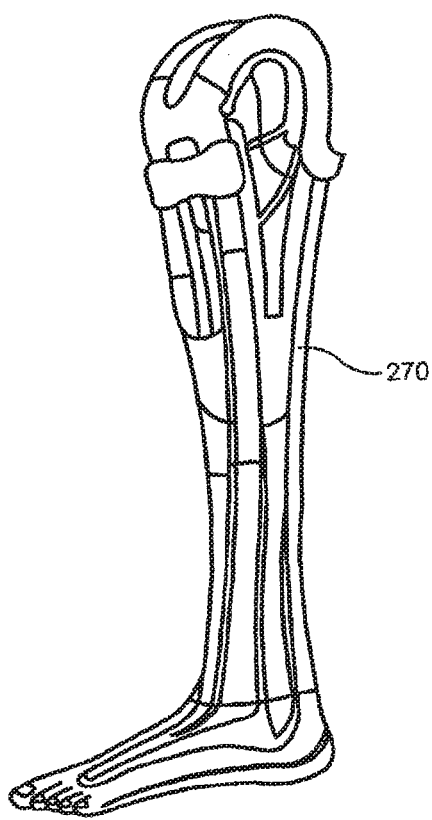
FIG. 23 is a perspective view of an example of a prosthetic socket having oval shaped struts 270 that extend past the socket and form a congruent pylon and foot system, representing an entire prosthesis.

FIG. 23 is a perspective view of an example of a prosthetic socket having oval shaped struts 270 that extend past the socket and form a congruent pylon and foot system, representing an entire prosthesis. Item 270 is a strut that serves as a strut for the socket as well as continuing down to form the keel of the foot thereby serving as an alignment component and terminal device a congruent unit that is also form contoured to match the needs of the amputee.

Figure 24:
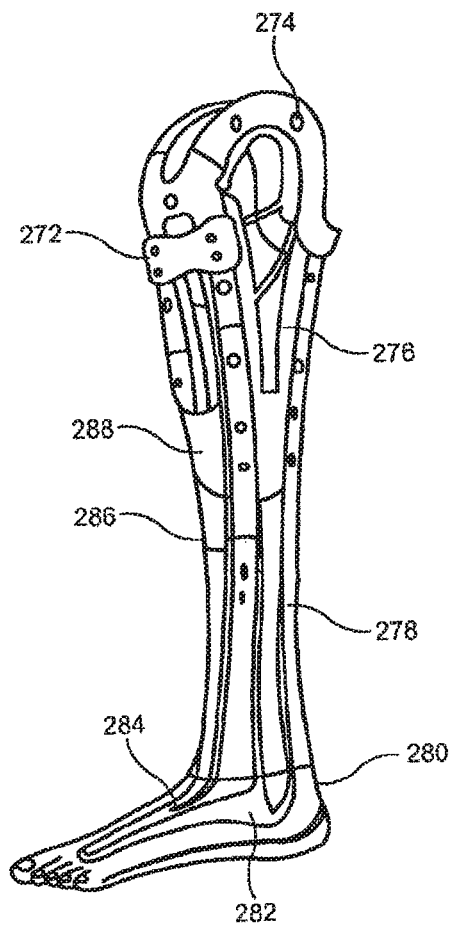
FIG. 24 is the same illustration as FIG. 23, except that it shows the option of having additional adjustment capabilities incorporated into the struts 278 and the interface members 272, 276, and 288.

FIG. 24 is the same illustration as FIG. 23, except that it shows the option of having additional adjustment capabilities incorporated into the struts 278 and the interface members 272, 276, and 288. More or less adjustability may be required, depending on the amount of volume fluctuation the individual typically experiences. Item 278 is a strut member with integrated adjustability. Item 286 is a height adjustability segment. Items 284, 280, and 282 show how the strut members may be contoured to transition directly into a prosthetic foot, to improve energy transfer and efficiency. Item 276 is an interfacing surface pad attached to the inside surface of the strut 278. Item 288 is a distal cup. Item 272 is an interface pad specially designed for the patellar tendon area of the socket. Item 274 is a proximal brim member for the medial aspect of the socket.

Figures 25, 26:
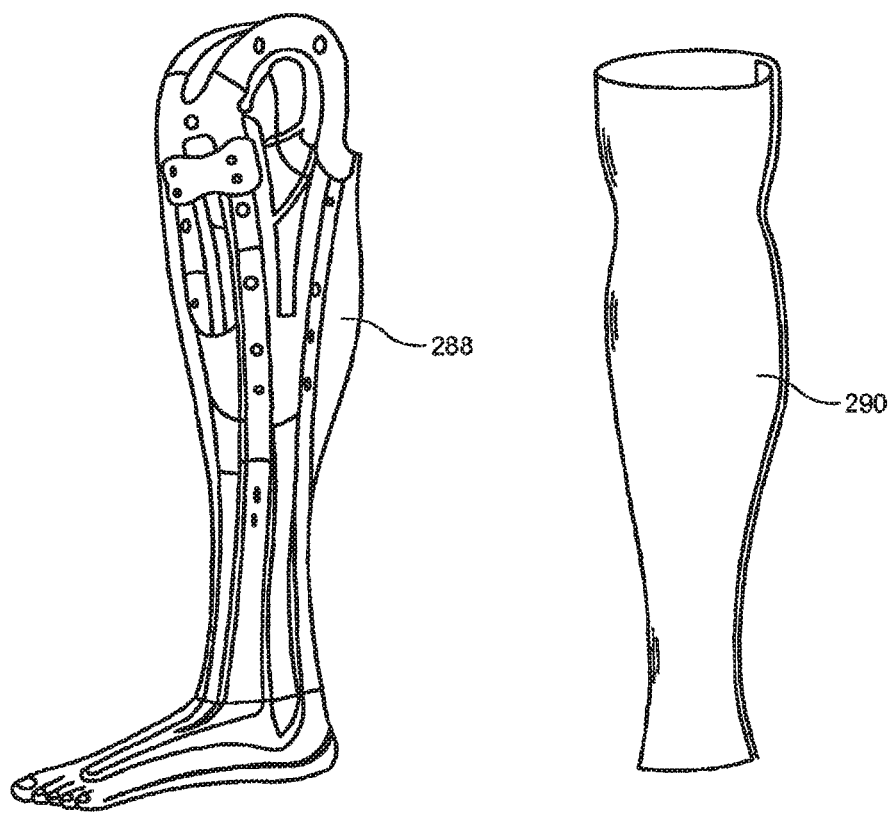
FIG. 25 depicts an embodiment similar to that in FIG. 23, except that it demonstrates with an outline that there is the option of having the entire modular prosthesis covered with a cosmetic covering or fairing 288.
FIG. 26 is a perspective view of a prefabricated wrap-around cosmetic cover 290.

FIG. 25 depicts an embodiment similar to that in FIG. 23, except that it demonstrates with an outline that there is the option of having the entire modular prosthesis covered with a cosmetic covering or fairing 288. Such a cosmetic cover or fairing 288 may be made of various types of materials and may achieve various objectives, such as protecting the inner parts or simply providing a stylish aesthetic. The cover or fairing 288 may be made as a custom or prefabricated addition.

FIG. 26 is a perspective view of a prefabricated wrap-around cosmetic cover 290. This example may be made of a thin, light, water resistant, and low-cost material such as polyethylene, and may easily be wrapped around, trimmed, and fixed to the finished prosthesis.

Figure 27:
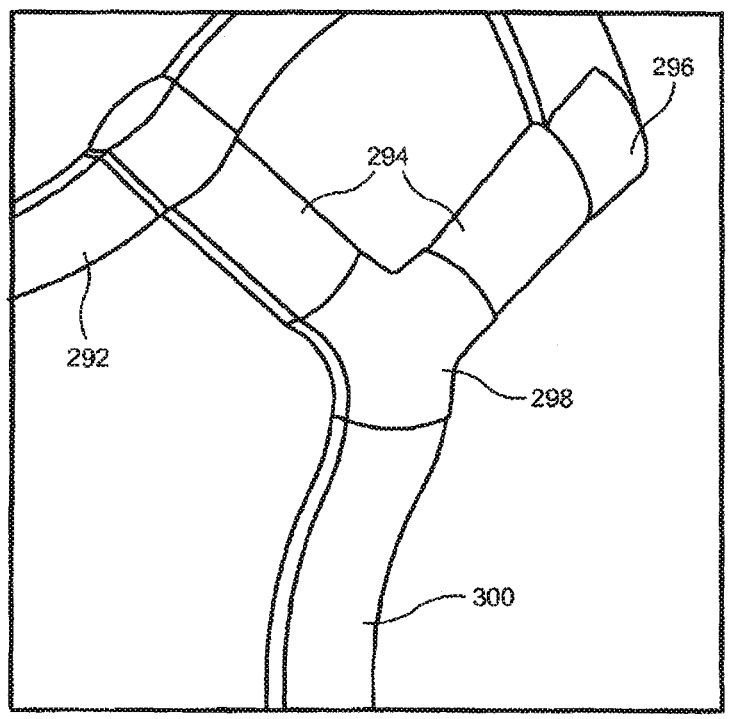
FIG. 27 is a perspective view of oval shaped struts 294 and 300, Y connecting joint member 298, proximal brim member 292, and proximal brim connector 296.

FIG. 27 is a perspective view of oval shaped struts 294 and 300, Y connecting joint member 298, proximal brim member 292, and proximal brim connector 296. These members make up a hypothetical example of modular members that may be selected and utilized for the lateral-proximal aspect of a trans-tibial prosthesis.

Figure 28:
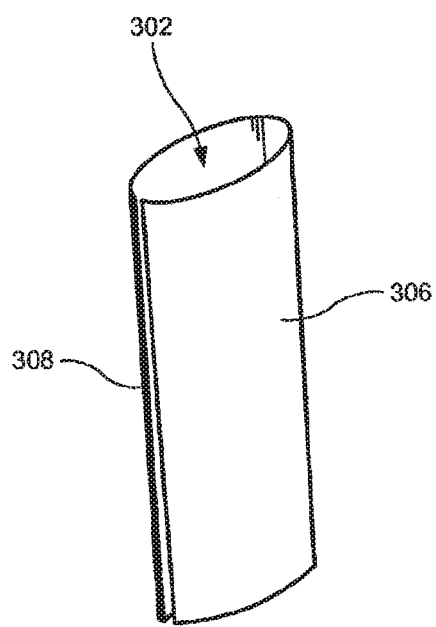
FIG. 28 is a perspective drawing of an oval shaped strut member.

FIG. 28 is a perspective drawing of an oval shaped strut member. Item 306 is the convex surface, designed for comfortable weight distribution, showing the rounded ends 308 that avoid any sharp edges. Item 302 is a hollow, solid, or filled core, depending on the needs.

Figure 29:
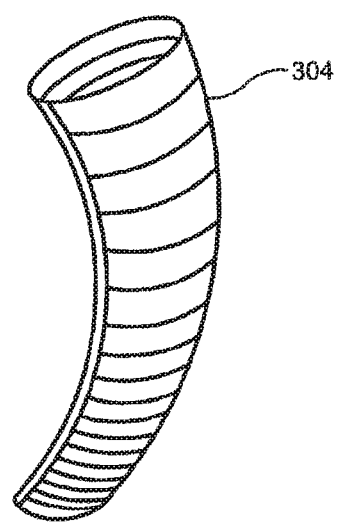
FIG. 29 is a perspective drawing of an oval shaped strut member 304 with contour and transverse plane rotation 304.

FIG. 29 is a perspective drawing of an oval shaped strut member 304 with contour and transverse plane rotation 304. Adjustability may come from the material used and/or from the mechanical design, and may remain flexible or be set rigid.

Figure 30:
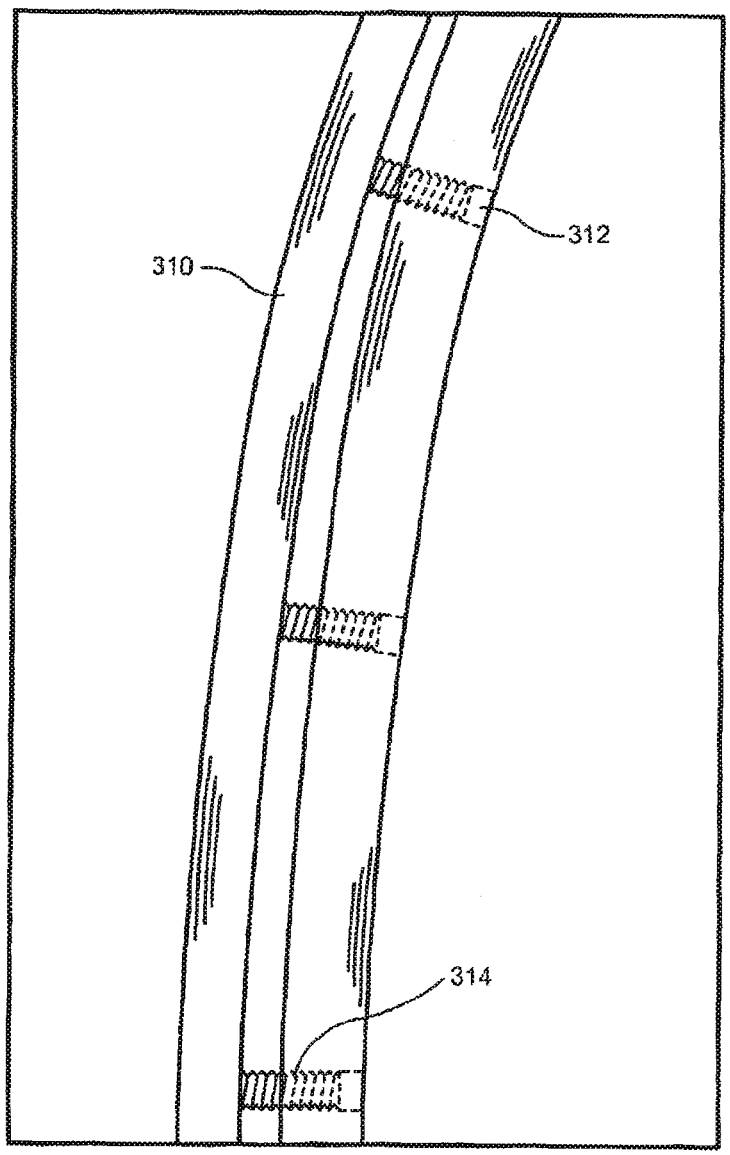
FIG. 30 is a lateral perspective of an oval shaped strut member 304 with contour and with adjustable interface member 310.

FIG. 30 is a lateral perspective of an oval shaped strut member 304 with contour and with adjustable interface member 310. Item 314 is an example of a set screw that may be used to tighten or loosen the compression of the interface member 310. Access 312 to the set screws 314 allows for easy adjustment by the user or the practitioner. A modular and adjustable interface member such as this may be applied to different members of the socket and may be utilized in various types of modular method sockets, as well as in other applications previously mentioned, such as orthotics, robotics, and exoskeletal applications.

Figure 31:
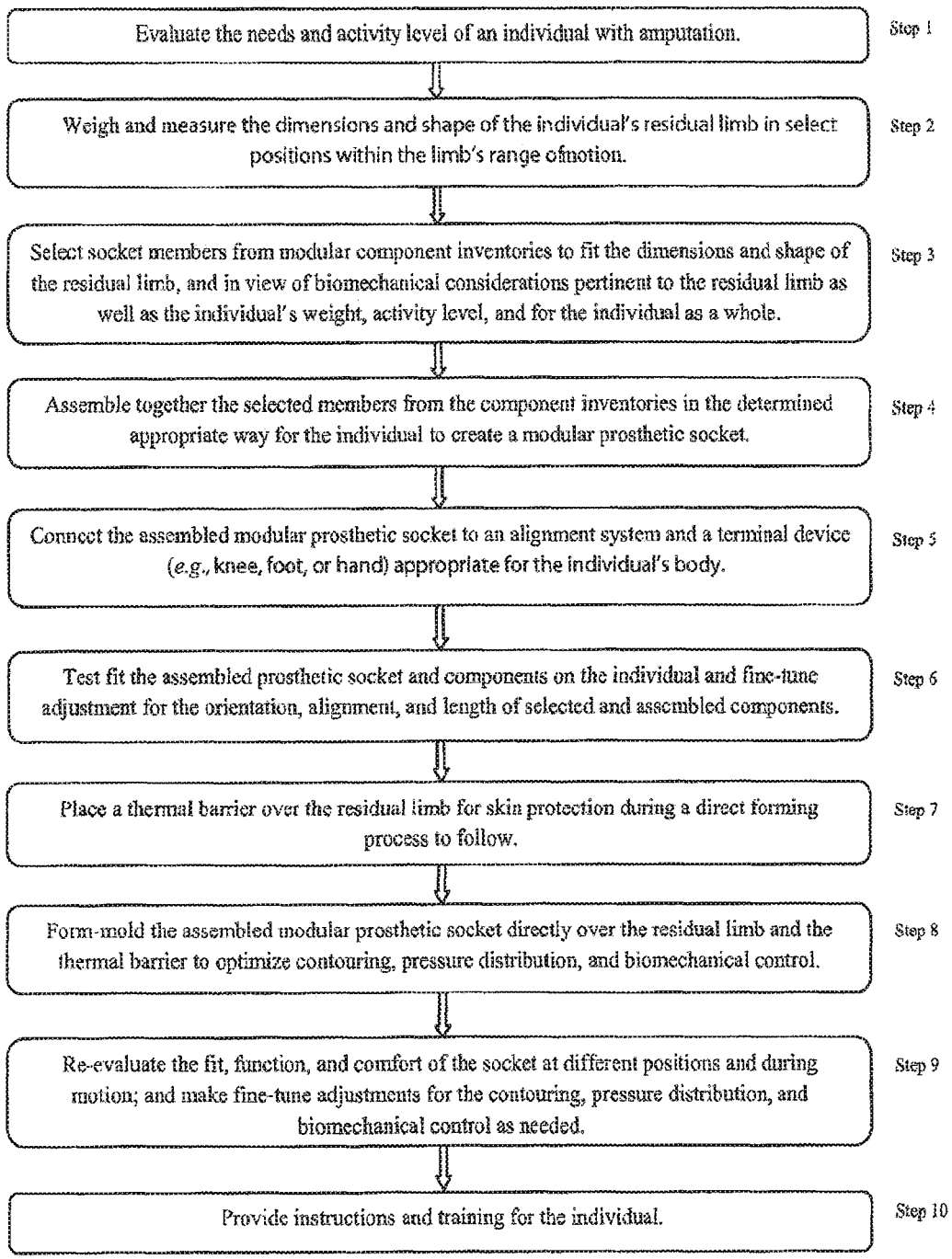
FIG. 31 is a flow chart showing an example of the steps involved in providing a prosthetic limb for an individual by the method for fitting a custom modular prosthetic socket according to the present invention.

FIG. 31 is a flow chart showing an example of the steps involved in providing a prosthetic limb for an individual by the method for fitting a modular prosthetic socket according to the present invention. In step 1 of this example, an evaluation of the individual with amputation is preformed wherein the evaluation includes questions and assessment that lead one trained in the field to be able to determine the activity level as well as gather the typical and desired acts of daily living for the individual with amputation. This information is important in ensuring that the modular prosthetic socket will be assembled with components that reflect the activity level of the individual and will facilitate the specific tasks and activities the individual performs or aims to perform. Step 2 includes weighing the individual and measuring the dimensions and shape of the individual's residual limb in select positions within the limb's range of motion. Step 2 is preformed in order to establish the size and contours of the residual limb through different positions in the limb's range of motion. The individual is weighted because it is important that the selected modular socket members are weight rated high enough for the individual's weight and activity level. Other evaluation parameters include; manual muscle testing, range of motion, skin condition, health history, allergies, sensitive areas or aspects to the residual limb, expectations and concerns, cosmetic preferences, therapy history and plan, psychological wellbeing, living condition, and other appropriate evaluation parameters. In step 3 socket members are selected from modular component inventories for their appropriateness with respect to the evaluation, measurements, and observation preformed in steps 1 and 2 wherein the component inventories are inventories that are separated by level of amputation and may include variation with respect to length, width, contour, flexibility, elastic modulus, durometer, formability, re-formability, adjustability, and other variation. For example, when fitting an individual who has had a trans-radial amputation one would refer to a modular prosthetic component kit that is specific to trans-radial level amputation wherein the kit includes struts of various width and weight ratings as determined by their strength, distal cups of various diameter, and various proximal brim styles. In step 4 the modular members that have been selected for the individual are to be assembled in such a way that is reflective of what has been learned of the individual during evaluation steps 1 and 2. For example, two different individuals may be indicated for the same modular prosthetic socket components but require different assembly of those components that is indicative of differences in their limb contour such that one individual's limb contours more gradually and the other's is more abrupt. In step 5 the socket is socket is connected to distal components of the prosthesis. This step would be eliminated in versions of the present invention where the distal components are integrated into the same cohesive unit as the modular socket members as shown in FIGS. 23-25. In step 6 the assembled modular prosthetic socket are tried directly onto the residual limb as a 'test' fitting wherein this is considered a 'test' in that it is expected that adjustments and changes will likely be required to optimize the fit and biomechanical control for the individual. The 'test' fitting of step 6 may be a static fitting (without motion of the limb) or a dynamic fitting (where the limb is tested in motion as well as static) depending on how good the test fit is and the capabilities of the individual with the test fit socket. In step 7 the limb is protected with a thermal barrier. This step is applicable when a direct forming technique that is exothermic or thermoforming is to be utilized to direct mold the socket members over the individual's residual limb in steps to follow. A thermal barrier may be used as a precautionary measure even though materials may even be safe directly against the skin during thermoforming. In step 8 one or more of the members included in the modular prosthetic socket are direct formed over the residual limb of the individual wherein the direct fitting process may include positive pressure or negative pressure from one or more molding aid devices, use of a specialized jig, computer aided, other assistive devices, and/or from manually forming member/s to the individuals residual limb by hand. For example, a wrap-around and sealing suction molding member may be used that can wrap around and seal for a large variety of individuals and is transparent such that one trained in the field can still manually influence the shape of the molding by hand over the molding member. In step 9 the modular prosthetic socket is donned and used dynamically while further evaluation is used to determine any changes that are required to the modular prosthetic socket or to the prosthesis as a whole. Evaluation of the fit and function of the prosthesis can be done manually through methods in the field and/or with the aid of computer analysis which may include temporarily inserted force sensors in the socket or permanently integrated force sensors. Step 10 represents the start of ensuring that the individual is trained in care of the prosthesis, proper use of the prosthesis, and necessary follow-up for the prosthesis. This training may include referrals or internal cooperation with other healthcare professionals such as physical and occupational therapists to aid in training and rehabilitation for the individual.

The above description is included to illustrate the operation of preferred embodiments, and is not meant to limit the scope of the invention. The scope of the invention is limited only by the following claims. From the above discussion, many variations will be apparent to one skilled in the art that would yet be encompassed by the spirit and scope of the present invention.

What is claimed is:

1. A modular prosthetic socket device for a lower extremity residual limb of a patient, the device comprising:
    a distal attachment member;
    four longitudinal struts, each of the struts having a distal end and a proximal end, and each of the struts connected at its distal end to the distal attachment member;
    a cross-link member fixed to and connected between two of the four longitudinal struts;
    a proximal brim member comprising an adjustable encircling band fitted over the proximal ends of the four longitudinal struts; and
    an ischial seat extension coupled with the proximal end of one of the four longitudinal struts, wherein the ischial seat extension is configured to bear weight by fitting under an ischial tuberosity of the patient.

2. A device as in claim 1, further comprising multiple adjustable hinges, wherein each hinge is attached between a different one of the distal ends of the four longitudinal struts and the distal attachment member.

3. A device as in claim 1, wherein the ischial seat extension is fastened to the one of the four struts with adjustable screws.

4. A device as in claim 1, wherein each of the proximal ends of the four longitudinal struts comprises a joining mechanism for receiving the encircling band.

5. A device as in claim 1, further comprising a flexible liner arranged on an interior aspect of the socket.

6. A device as in claim 1, wherein the four struts are removably attached to the distal attachment member.

7. A device as in claim 1, wherein at least one of the struts comprises a reformed strut that was reformed from an initial shape to a reformed shape to better fit the residual limb of the patient.

8. A device as in claim 7, wherein the at least one reformed strut comprises a strut that was reformed by applying heat to the strut.

9. A device as in claim 8, wherein the at least one reformed strut comprises a strut that was reformed by directly molding the strut in its initial shape against the residual limb of the patient to reform the strut into the reformed shape.

10. A device as in claim 1, wherein the ischial seat extension comprises a shock absorbing silicone pad.

* * * * *